(12) United States Patent
Palsule et al.

(10) Patent No.: US 10,087,283 B2
(45) Date of Patent: Oct. 2, 2018

(54) POLYESTER MACROMERS CONTAINING 1,1-DICARBONYL-SUBSTITUTED 1 ALKENES

(71) Applicant: SIRRUS, INC., Loveland, OH (US)

(72) Inventors: Aniruddha Palsule, Cincinnati, OH (US); Jeffrey M. Sullivan, Goshen, OH (US); Kshitij K. Parab, Loveland, OH (US); Elliott King, Milford, OH (US); William Barrett, Bethel, OH (US)

(73) Assignee: SIRRUS, INC., Loveland, OH (US)

( * ) Notice: Subject to any disclaimer, the term of this patent is extended or adjusted under 35 U.S.C. 154(b) by 0 days.

(21) Appl. No.: 15/472,379

(22) Filed: Mar. 29, 2017

(65) Prior Publication Data

US 2017/0349702 A1 Dec. 7, 2017

Related U.S. Application Data

(63) Continuation of application No. 15/437,164, filed on Feb. 20, 2017, now Pat. No. 9,745,413, which is a
(Continued)

(51) Int. Cl.
*C08G 63/60* (2006.01)
*C08G 64/42* (2006.01)
(Continued)

(52) U.S. Cl.
CPC ............ *C08G 63/60* (2013.01); *C07C 69/593* (2013.01); *C08G 64/42* (2013.01); *C12P 7/62* (2013.01)

(58) Field of Classification Search
None
See application file for complete search history.

(56) References Cited

U.S. PATENT DOCUMENTS 2,212,506 A 8/1940 Bachman
2,245,567 A 6/1941 Brant et al.
(Continued)

FOREIGN PATENT DOCUMENTS

CN 102901754 A 1/2013
DE 19508049 A1 9/1996
(Continued)

OTHER PUBLICATIONS

Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.
(Continued)

*Primary Examiner* — Vu A Nguyen
(74) *Attorney, Agent, or Firm* — Young Basile Hanlon & MacFarlane, P.C.

(57) ABSTRACT

Disclosed are compositions comprising polyester macromers containing in one or more chains the residue of one or more diols and one or more diesters wherein the residue of the one or more diols and the one or more diesters alternate along the chain and a portion of the diesters are 1,1-diester-1-alkenes, and optionally one or more dihydrocarbyl dicarboxylates, and at least one terminal end comprises the residue of one of the 1,1-diester-1 alkenes and wherein one or more terminal ends may comprise the residue of one or more diols. The chains may contain the residue of the one or more diols and one or more diesters comprising one or more diesters 1,1-diester-1 alkenes and optionally one or more dihydrocarbyl dicarboxylates randomly disposed along the chains. Disclosed are methods of preparing the polyester macromers and incorporating them in a variety of polyester containing compositions such as coatings and films.

19 Claims, 2 Drawing Sheets

Related U.S. Application Data continuation of application No. 15/234,191, filed on Aug. 11, 2016, now Pat. No. 9,617,377.

(60) Provisional application No. 62/345,334, filed on Jun. 3, 2016.

(51) Int. Cl.
 *C07C 69/593* (2006.01)
 *C12P 7/62* (2006.01)

(56) References Cited

U.S. PATENT DOCUMENTS

| | | |
|---|---|---|
| 2,403,791 A | 7/1941 | D'Aiello |
| 2,277,479 A | 3/1942 | D'Aiello |
| 2,313,501 A | 3/1943 | Bachman et al. |
| 2,330,033 A | 9/1943 | D'Aiello |
| 3,042,710 A | 7/1962 | Dickstein et al. |
| 3,197,318 A | 7/1965 | Halpern et al. |
| 3,203,915 A | 8/1965 | D'Aiello |
| 3,221,745 A | 12/1965 | Coover et al. |
| 3,427,250 A | 2/1969 | Haas et al. |
| 3,489,663 A | 1/1970 | Bayer et al. |
| 3,523,097 A | 8/1970 | Coover et al. |
| 3,557,185 A | 1/1971 | Ito et al. |
| 3,591,676 A | 7/1971 | Hawkins |
| 3,595,869 A | 7/1971 | Shuman |
| 3,677,989 A | 7/1972 | Jenkinson |
| 3,758,550 A | 9/1973 | Eck et al. |
| 3,923,836 A | 12/1975 | Bender |
| 3,936,486 A | 2/1976 | Egger et al. |
| 3,940,362 A | 2/1976 | Overhurlts |
| 3,945,891 A | 3/1976 | Aal et al. |
| 3,966,562 A | 6/1976 | Mukushi et al. |
| 3,975,422 A | 8/1976 | Buck |
| 3,978,422 A | 8/1976 | Rheinfelder |
| 3,995,489 A | 12/1976 | Smith et al. |
| 4,001,345 A | 1/1977 | Gorton et al. |
| 4,004,984 A | 1/1977 | Margen |
| 4,018,656 A | 4/1977 | Rogers et al. |
| 4,035,243 A | 7/1977 | Katz et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Arni et al. |
| 4,140,584 A | 2/1979 | Margen |
| 4,148,693 A | 4/1979 | Williamson |
| 4,154,914 A | 5/1979 | Kuraya |
| 4,160,864 A | 7/1979 | Ponticello et al. |
| 4,176,012 A | 11/1979 | Bryant |
| 4,186,058 A | 1/1980 | Katz et al. |
| 4,186,060 A | 1/1980 | Katz et al. |
| 4,198,334 A | 4/1980 | Rasberger |
| 4,224,112 A | 9/1980 | Childs |
| 4,229,263 A | 10/1980 | Childs |
| 4,236,975 A | 12/1980 | Childs |
| 4,237,297 A | 12/1980 | Rody et al. |
| 4,243,493 A | 1/1981 | Gruber et al. |
| 4,256,908 A | 3/1981 | Nishimura et al. |
| 4,282,067 A | 8/1981 | Katz et al. |
| 4,282,071 A | 8/1981 | Sherrod |
| 4,291,171 A | 9/1981 | Baum et al. |
| 4,313,865 A | 2/1982 | Teramoto et al. |
| 4,319,964 A | 3/1982 | Katz et al. |
| 4,329,479 A | 5/1982 | Yabutani et al. |
| 4,396,039 A | 8/1983 | Klenk et al. |
| 4,399,300 A | 8/1983 | Prange et al. |
| 4,411,740 A | 10/1983 | Flanigam et al. |
| 4,440,601 A | 4/1984 | Katz et al. |
| 4,440,910 A | 4/1984 | O'Connor |
| 4,443,624 A | 4/1984 | Prange et al. |
| 4,444,928 A | 4/1984 | Karrer |
| 4,450,067 A | 5/1984 | Angevine et al. |
| 4,503,074 A | 3/1985 | Friedman |
| 4,504,658 A | 3/1985 | Narisada et al. |
| 4,510,273 A | 4/1985 | Miura et al. |
| 4,517,105 A | 5/1985 | Laemmle et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,727,701 A | 3/1988 | Figari |
| 4,728,701 A | 3/1988 | Jarvis et al. |
| 4,736,056 A | 4/1988 | Smith et al. |
| 4,767,503 A | 8/1988 | Crescentini et al. |
| 4,769,464 A | 9/1988 | Sajtos |
| 4,783,242 A | 11/1988 | Robbins |
| 4,835,153 A | 5/1989 | Kabota et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,064,507 A | 11/1991 | O'Donnell |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,259,835 A | 11/1993 | Clark et al. |
| 5,284,987 A | 2/1994 | Sikkenga et al. |
| 5,292,937 A | 3/1994 | Manning et al. |
| 5,328,687 A | 4/1994 | Leung et al. |
| 5,312,864 A | 5/1994 | Wenz et al. |
| 5,334,747 A | 8/1994 | Steffen |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 11/1996 | Song |
| 5,575,997 A | 11/1996 | Leung et al. |
| 5,582,834 A | 12/1996 | Leung et al. |
| 5,614,650 A | 3/1997 | Sandler et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,054,606 A | 4/2000 | Irie et al. |
| 6,069,261 A | 5/2000 | Hoffmann et al. |
| 6,096,848 A | 8/2000 | Gololobov et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |
| 6,211,273 B1 | 4/2001 | Bru-Magniez et al. |
| 6,225,038 B1 | 5/2001 | Smith et al. |
| 6,238,896 B1 | 5/2001 | Ozaki et al. |
| 6,245,933 B1 | 6/2001 | Malofsky et al. |
| 6,284,915 B2 | 9/2001 | Hirase et al. |
| 6,291,703 B1 | 9/2001 | Schaerfl et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,518,677 B1 | 2/2003 | Capote |
| 6,545,097 B2 | 4/2003 | Pinchuk et al. |
| 6,559,264 B1 | 5/2003 | Konig et al. |

(56) References Cited

U.S. PATENT DOCUMENTS

| | | |
|---|---|---|
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,716,355 B1 | 4/2004 | Hanemaaijer et al. |
| 6,750,298 B1 | 6/2004 | Bru-Magniez et al. |
| 6,794,365 B2 | 9/2004 | Al-Obeidi et al. |
| 6,841,064 B1 | 1/2005 | Weiss et al. |
| 6,936,140 B2 | 8/2005 | Paxton et al. |
| 7,070,675 B2 | 7/2006 | Schmidt et al. |
| 7,109,369 B2 | 9/2006 | Nose et al. |
| 7,208,621 B2 | 4/2007 | Nose et al. |
| 7,226,957 B1 | 6/2007 | Scranton et al. |
| 7,305,850 B2 | 12/2007 | Tonkovich et al. |
| 7,553,989 B2 | 6/2009 | Sawabe et al. |
| 7,603,889 B2 | 10/2009 | Cypes et al. |
| 7,610,775 B2 | 11/2009 | Tonkovich et al. |
| 7,649,108 B2 | 1/2010 | Schal et al. |
| 7,659,423 B1 | 2/2010 | McArdle |
| 7,663,000 B2 | 2/2010 | Dekkers et al. |
| 7,771,567 B2 | 8/2010 | Rives et al. |
| 7,829,738 B1 | 11/2010 | Brammer et al. |
| 7,900,558 B2 | 3/2011 | Yokoi |
| 8,425,999 B2 | 4/2013 | McArdle et al. |
| 8,609,885 B2 | 12/2013 | Malofsky et al. |
| 8,884,051 B2 | 11/2014 | Malofsky et al. |
| 9,108,914 B1 | 8/2015 | Malofsky et al. |
| 9,181,365 B2 | 11/2015 | Malofsky et al. |
| 9,217,098 B1 | 12/2015 | Stevenson et al. |
| 9,221,739 B2 | 12/2015 | Malofsky et al. |
| 9,234,107 B2 | 1/2016 | Malofsky et al. |
| 9,334,430 B1 | 5/2016 | Stevenson et al. |
| 9,481,640 B2 | 11/2016 | McArdle et al. |
| 9,745,413 B1 * | 8/2017 | Palsule .......... C08G 63/52 |
| 2001/0005572 A1 | 6/2001 | Lobo et al. |
| 2001/0034300 A1 | 10/2001 | Yurugu et al. |
| 2002/0035231 A1 | 3/2002 | Whitehouse et al. |
| 2002/0143128 A1 | 10/2002 | Cabioch et al. |
| 2002/0151629 A1 | 10/2002 | Buffkin et al. |
| 2003/0096069 A1 | 5/2003 | D'Alessio |
| 2003/0199655 A1 | 10/2003 | Yurugi et al. |
| 2004/0057914 A1 | 3/2004 | Bonda et al. |
| 2004/0076601 A1 | 4/2004 | Bru-Magniez et al. |
| 2004/0082043 A1 | 4/2004 | Yadav et al. |
| 2004/0220060 A1 | 11/2004 | Bartley et al. |
| 2006/0167267 A1 | 7/2006 | Chorghade et al. |
| 2006/0211809 A1 | 9/2006 | Kodemura et al. |
| 2007/0043145 A1 | 2/2007 | Beck et al. |
| 2007/0049655 A1 | 3/2007 | Yoshimune et al. |
| 2007/0092483 A1 | 4/2007 | Pollock |
| 2007/0120630 A1 | 5/2007 | Huang et al. |
| 2007/0238872 A1 | 10/2007 | Sabesan |
| 2008/0131618 A1 | 6/2008 | Nakamura et al. |
| 2008/0160305 A1 | 7/2008 | Warren et al. |
| 2008/0187655 A1 | 8/2008 | Markle et al. |
| 2008/0227919 A9 | 9/2008 | Li et al. |
| 2008/0241485 A1 | 10/2008 | Shimohara et al. |
| 2008/0286333 A1 | 11/2008 | Kangas et al. |
| 2009/0203861 A1 | 8/2009 | Lee et al. |
| 2009/0263604 A1 | 10/2009 | Arai et al. |
| 2010/0016508 A1 | 1/2010 | Sasagawa et al. |
| 2010/0256720 A1 | 10/2010 | Overstreet et al. |
| 2010/0286433 A1 | 11/2010 | Malofsky et al. |
| 2010/0286438 A1 | 11/2010 | Malofsky et al. |
| 2011/0015406 A1 | 1/2011 | Umentani et al. |
| 2011/0024392 A1 | 2/2011 | Sato et al. |
| 2011/0164322 A1 | 7/2011 | Morozumi et al. |
| 2012/0083523 A1 | 4/2012 | Richard et al. |
| 2012/0136130 A1 | 5/2012 | Takashima et al. |
| 2012/0203021 A1 | 8/2012 | Friese et al. |
| 2013/0019520 A1 | 1/2013 | Sello et al. |
| 2013/0281580 A1 | 10/2013 | Malofsky et al. |
| 2013/0303719 A1 | 11/2013 | Malofsky et al. |
| 2013/0324754 A1 | 12/2013 | Bredsguard |
| 2014/0058031 A1 | 2/2014 | Overbeek et al. |
| 2014/0248485 A1 | 9/2014 | Malofsky et al. |
| 2014/0275400 A1 | 9/2014 | Chen et al. |
| 2014/0288230 A1 | 9/2014 | Malofsky et al. |
| 2014/0329980 A1 * | 11/2014 | Malofsky .......... C09J 133/06 526/309 |
| 2015/0056879 A1 | 2/2015 | Malofsky et al. |
| 2015/0104660 A1 | 4/2015 | Malofsky et al. |
| 2015/0148480 A1 | 5/2015 | Ellison et al. |
| 2015/0210894 A1 | 7/2015 | Malofsky et al. |
| 2015/0303122 A1 | 10/2015 | Malofsky et al. |
| 2015/0361283 A1 | 12/2015 | Malofsky et al. |

FOREIGN PATENT DOCUMENTS

| | | |
|---|---|---|
| EP | 2768917 A2 | 2/2009 |
| FR | 2788516 A1 | 7/2000 |
| GB | 432628 A | 7/1935 |
| GB | 965676 | 8/1964 |
| GB | 965767 | 8/1964 |
| GB | 975733 | 11/1964 |
| JP | S56-081537 A | 7/1981 |
| JP | H02281013 | 11/1990 |
| JP | H08231564 | 9/1996 |
| JP | 09258448 A | 10/1997 |
| JP | 2000199936 A | 7/2000 |
| JP | 2003201397 A | 7/2003 |
| JP | 2008174494 | 1/2007 |
| WO | 1999/046619 | 9/1999 |
| WO | 1999/055394 A1 | 9/1999 |
| WO | 2007/120630 A2 | 10/2007 |
| WO | 2010/091975 A1 | 8/2010 |
| WO | 2010/129068 A1 | 11/2010 |
| WO | 2011/059104 A1 | 5/2011 |
| WO | 2011/161045 A1 | 12/2011 |
| WO | 2012/054616 A2 | 4/2012 |
| WO | 2012/054633 A2 | 4/2012 |
| WO | 2013/059473 | 4/2013 |
| WO | 2013/066629 | 5/2013 |
| WO | 2013/149165 A1 | 10/2013 |
| WO | 2013/149168 A1 | 10/2013 |
| WO | 2013/149173 A1 | 10/2013 |

OTHER PUBLICATIONS

McNab, Kirk-Othmer Encyclopedia of chemical Technology, Pyrolysis, Flash Vacuum, 2009, John Wiley & Sons, Inc., pp. 1-26.

Block, "Diethyl bis (hydroxymethyl) malonate "Organic Syntheses, 1973, Coll. vol. 5, p. 381 [vol. 40, p. 27 (1960); Retrieved on Apr. 4, 2014 from internet: http://www.Orgsyn.org/content/pdfs/procedures/cv5p0381.pdf] p. 381, para 1.

Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.

M. Ware et al.: "DBU: An Efficient Catalyst for Knoeveganel Condensation under Solvent-free Condition," Bulletin of the Catalysis Society of India, (2007), vol. 6, pp. 104-106.

V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.

J. S. Yadav et al.: "Phosphane-Catalyzed Knoevenagel Condensation: a Facile Synthesis of a-Cyanoacrylates and a-Cyanoacrylonitriles," Eur, J, Org, Chem. (2004), pp. 546-551.

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.

H, A, Oskooie et al.: "On Water: an Efficient Knoevenagel Condensation using 12-Tungstophosphoric Acid as a Reusable Green Catalyst," Synthetic Communications, (2006), vol. 36, pp. 2819-2823.

H. Jiang et al.: "Inorganic Zinc Salts Catalyzed Knoevenagel Condensation at Room Temperature without Solvent," Preparative Biochemistry & Biotechnology, (2009), vol. 39, pp. 194-200.

(56) References Cited

OTHER PUBLICATIONS

T. Doi et al.: "Synthesis of Dimethyl gloiosiphne A by Way of Palladium-Catalyzed Domino Cyclization," T. Ora <htto://T.Ora>. Chem., (2007), vol. 72, pp. 3667-3671.

H. Jung et al,: "New and General Methods for the Synthesis of Arylmethylene Bis(3- Hydroxy- 2-Cyclohexene-l-Ones) and Xanthenediones by EDDA and ln(OTf)3-Catalyzed One-Pot Domino Knoevenagei/Michael or Koevenagei/Michaei/Cyclodehydration Reactions," Bull. Korean Chem. Soc. (2009) vol. 30, No. 9, pp. 1989-1995.

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarwczyk: "A General Synthesis of 1,1 Disubstituted Electron Deficient Olefins and their Polymer Properties," Polymer,- (1998), vol. 39, No. I, pp. 173-181.

Gill, Charansingh, et al. "Knoevenagel condensation in neutral media: A simple and efficient protocol for the synthesis of electrophillic alkenes catalyzed by anhydrous ferric sulphate with remarkable reusability." Bulletin of the Catalysis Society of India 7 (2008): 153-157.

P, Ballesteros et al.: "D 1-tert-Butyl Methylenemalonate [Propanedioic Acid, Methylene-, bis( 1,1-dimethylethyl)ester]," Organic Syntheses. Coli. (1990), vol. 7, p. 142; (1986) vol. 64, p. 63.

A. M. Vetrova et al.: "Improvement of the Thermal Stability of Cyanoacrylate Adhesives," Polymer Science, Series D, (2009), vol. 2, No. 1, pp. 27-30.

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.

G. Lai et al.: "Ionic Liquid Functionalized Silica Gel: Novel Catalyst and Fixed Solvent," Tetrahedron Letters (2006), vol. 47, pp. 6951-6953.

J. R. Harjani et al.: "Lewis Acidic Ionic Liquids for the Synthesis of Electrophilic Alkenes; via the Knoevenagel Condensation," Tetrahedron Letters, (2002), vol. 43, pp. 1127-1130.

P. Ballesteros et al.: "Synthesis of Dl-tent-Butyl Methylenemalonate, a Sterically Hindered 1,1-Dicarbonyl Alkene," J. Ora <htto://J. Ora>. Chem, (1983), vol. 48, pp. 3603-3605.

M. Matziari et al. Active Methylene Phosphinic Peptides: A new Diversification Approach Organic Letters 2006 vol. 8, No. 11 pp. 2317-2319 May 5, 2006.

Zaragoza Dorwald, Side Reactions in Organic Synthesis, 2005, Wiley-VCH Verlag GmbH & Co., KgaA, Weinheim, Preface. p. IX.

K. Okamura and T. Date, A Facile Conversion of Ethoxydihydropyrans to 4-Cyanoethylisoxazoles, J. Heterocyclic Chem. 33, 383 (1996).

Yamauchi et al. Tetrahedron Asymetry 12, (2001), 3113-3118.

Cristoph Schotes et al. "Cu(I)- and C(II)- Catalyzed Cyclo- and Michael Addition Reactions of Unsaturated [beta]-Ketoesters" The Journal of Organic Chemistry, vol. 76, No. 14 dated Jul. 15, 2011 p. 5862-5866.

Alejandro Bugarin et al. "Efficient direct [alpha]-methylenation of carbonyls mediated by dissopropylammonium trifluoroacetate", Chemical Communications, vol. 46, No. 10 dated Jan. 25, 2010.

H. Hoffman et al. "Preparation and Selected Reaction of tery-Butyl 2-Methylene-3-oxoalkanoates" Chem. Ber., vol. 124 dated Jan. 1, 1991, pp. 2475-2480.

M. Yamauchi et al. "Reactivity of 2-Methylene-1, 3-dicarbonyl Compounds. 1,3-Dipolar Cycloaddition Reaction with Ethyl Diazoacetate", Chem. Pham. Bull., vol. 49, No. 12, dated Jun. 25, 2001, pp. 1638-1639.

Lawrence N J et al. "Reaction of Baylis-Hillman products with Swern and Dess-Martin oxidants", Tetrahedron Letters, Pergamon, GB, vol. 42 No. 23 dated Jun. 4, 2001, pp. 3939-3941.

Juliana Vale et al. "Efficient [alpha]-Methylenation of Carbonyl Compounds in Ionic Liquids at Room Temperature", Synlett, vol. 2009, No. 01, Jan. 1, 2009 (Jan. 1, 2009), pp. 75-78, XP055170349, ISSN: 0936-5214, DOI: 10.1055/s-0028-1087389 *table 2; compound 3 *.

P. Breton et al., "New Poly(Methylidudene Malonate 2.1.2) Nanoparticles: Recent Developments", Targeting of Drugs 4, NATO ASI Series, vol. 273, pp. 161-172, 1994.

Limouzin et al., "Anionic Polymerization of n-Butyl Cyanoacrylate in Emulsion and Miniemulsion" Macromolecules, vol. 36, 2003, pp. 667-674.

McCoy, M. "A New Way to Stick" Chemical & Engineering News, vol. 92, Issue 26, Jun. 30, 2014, pp. 17-18, paragraph [2].

Bachman et al., "Diethyl Methylenemalonate" Contirbution from the Research Laboratories of the Eastman Kodak Company, May 17, 1939, pp. 493-501.

"Knoevenagel reaction on a molecular sieve", Li Qifang et al., Chinese Science Bulletin, vol. 12, pp. 914-917. (1988).

"Knoevenagel Condensation Over Acidic Zeolite", Zuo Bojun et al., Chinese Journal ofCatalysis, vol. 23 (6), pp. 555-558. (2002).

"Comparison of the catalytic activity of MOFs and zeolites in Knoevenagel condensation", Maksym Opanasenko, et al., Catalysis Science & Technology, vol. 3 p. 500-507. (2013).

Corey et al. "Total Synthesis of Gibberellic Acid. A Simple Synthesiss of a Key Intermediate", J. Am. Chem. Soc. 1982, 104, 6129-6130.

Krishna et al. "Stereodefined Access to 3-Deoxy Sugars Through a Tandem Baylis-Hillman and Lewis Acid Catalyzed Sequence", European Journal of Organic Chemistry, 2010, 813-817.

March, *Advanced Organic Chemistry*, 2d Ed, section 0-25, pp. 365-367, 1977, McGraw Hill, New York, New York.

Morrison and Boyd, *Organic Chemistry*, $4^{th}$ Ed., pp. 831 and 836-838, 1983, Allyn Bacon, Inc., Boston, MA.

Otera et al., "Esterification: Methods, Reactions, and Applications", $2^{nd}$ Ed., pp. 55-58, 2010, Wiley-VCH Verlag Gmbh & Co. KGaA. Weinheim, Germany.

"Esterification of Sludge Palm Oil Using Trifluromethanesulfonic Acid for Preparation of Biodiesel Fuel", Korean Journal of Chemical Engineering, Jun. 2013, vol. 30, issue 6, pp. 1229-1234.

Transsesterification of diethyl malonate with Benzyl Alcohol Catalyzed by Modified Zirconia: Kinetic Study, Journal of Molecular Catalysis A: Chemical, vol. 391, Sep. 2014, pp. 55-65.

Olah et al., "Superelectrophilic Solvation," Accounts of Chemical Research, Apr. 2004, vol. 37, No. 4.

Kütt et al., "Equilibrium Acidities of Superacids," Journal of Organic Chemistry, vol. 76, No. 2, 2011, pp. 391-395, published on the web Dec. 17, 2010.

Larras et al. Synthesis and micellization of amphiphilic poly(ethylene oxide)-block-poly(methylidene malonate 2.1.2.) diblock copolymers Macromol. Rapid Commun. dated2000, vol. 21, pp. 1089-1029.

* cited by examiner

Figure 1: Gloss Meter Analysis:
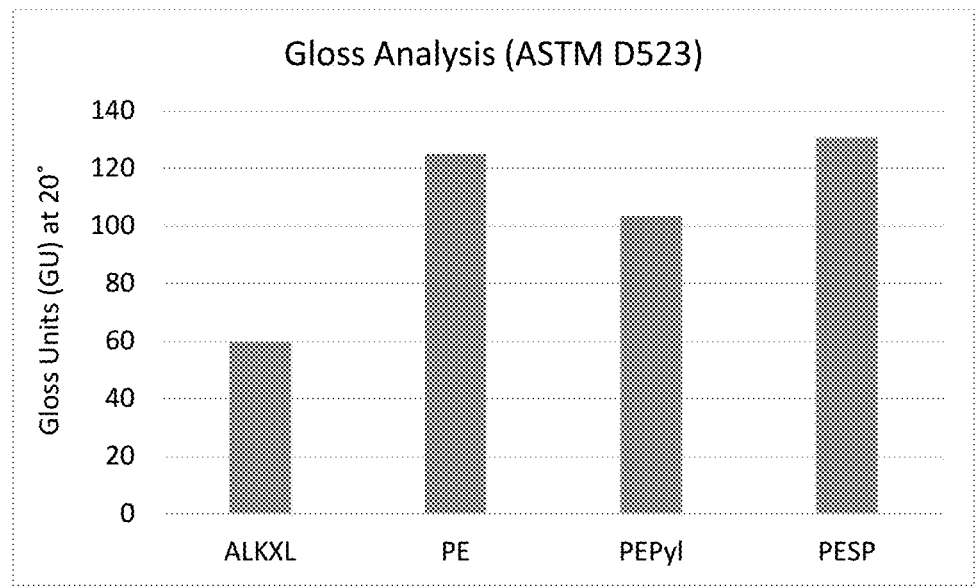
Figure 2: Solvent resistance of MEK wipes:
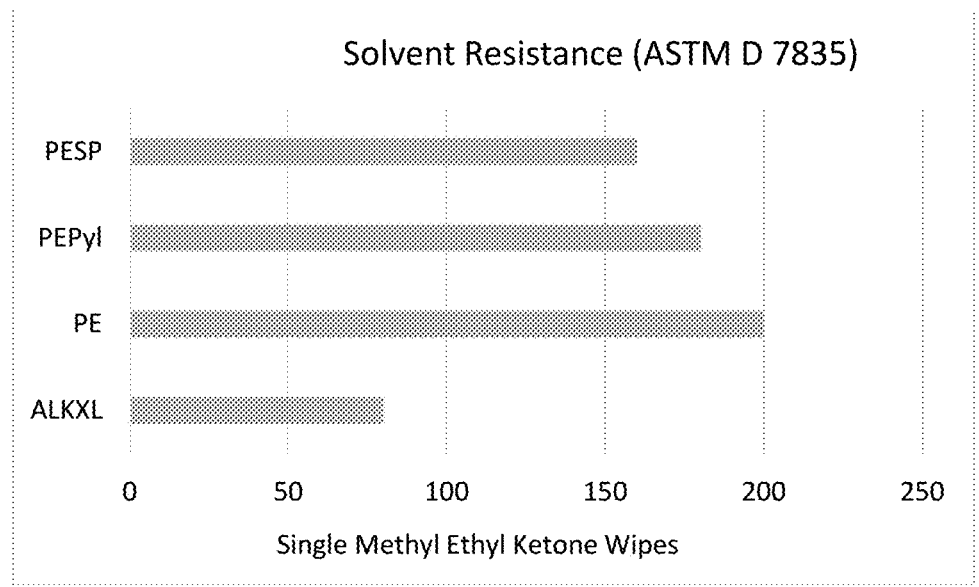

Figure 3; Pencil hardness test results:
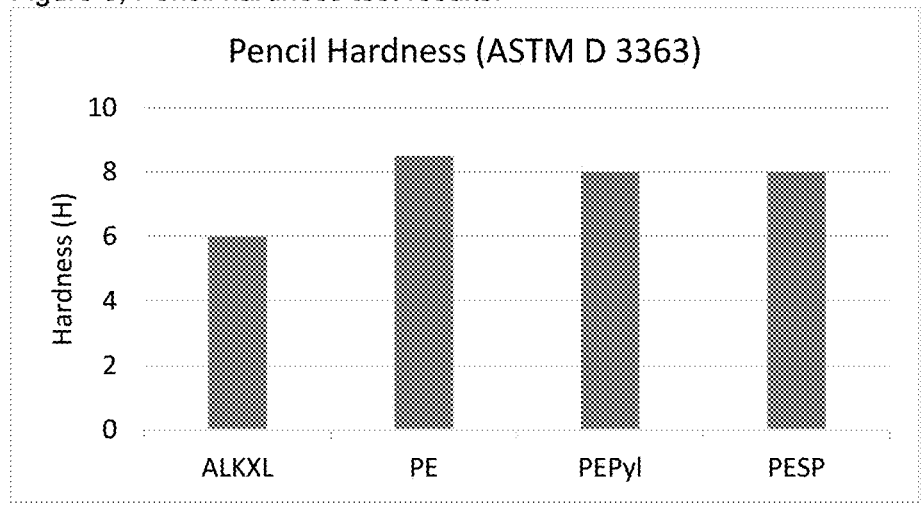

POLYESTER MACROMERS CONTAINING 1,1-DICARBONYL-SUBSTITUTED 1 ALKENES

FIELD

Disclosed are novel compounds and compositions containing polyester macromers containing the residue of 1,1-diester-1-alkene compounds. Further disclosed are methods for the preparation of the novel compounds and compositions.

BACKGROUND

Polyesters are utilized in a number of applications due to their properties and their ease of synthesis. Exemplary uses include coatings, films, fibers, and resins. Due to their properties polyesters are also utilized in blends with other polymers to improve certain property limitations of the other polymers, such polymers include polycarbonates, polyamides, styrenic polymers, and polyolefins, and the like. Polyesters are typically prepared by reacting diesters with dialcohols, and generally are linear in structure. It is somewhat challenging to cross-link these polyesters due the structure. Some crosslinking processes require special catalysts or high temperatures.

1,1-diester-1-alkenes, such as methylene malonates, contain two diester groups, and an alkylene group disposed between the two diester groups. Recent developments in synthesis of these compounds facilitate the synthesis of these compounds and their use in a variety of applications, see Malofsky U.S. Pat. No. 8,609,885; U.S. Pat. No. 8,884,051; and U.S. Pat. No. 9,108,914; incorporated herein by reference in their entireties for all purposes. Processes for transesterifying these compounds have also been recently developed. Malofsky et al. WO 2013/059473, US 2014/0329980, incorporated herein by reference in their entirety for all purposes, discloses the preparation of multifunctional methylene malonates by multiple synthetic schemes. One disclosed process involves reacting a methylene malonate with a polyol in the presence of a catalyst to prepare compounds wherein one of the ester groups on the methylene malonates undergoes transesterification to react with the polyol and form multifunctional compounds (multifunctional meaning the presence of more than one methylene malonate core unit). The use of enzyme catalysis is disclosed. Sullivan, U.S. Pat. No. 9,416,091 discloses transesterification of 1,1-disubstituted-1-alkenes using certain acid catalysts, incorporated herein by reference in its entirety for all purposes.

What is needed are compositions useful in preparing polyesters which can be crosslinked elegantly without the need for problematic catalysts and which use relatively mild conditions. Coatings prepared from such compositions that exhibit enhanced properties are needed, such enhanced properties include flexibility, adhesion to substrates, pencil hardness, solvent resistance, abrasion resistance, ultraviolet ray resistance, high temperature acid and base resistance, and the like. Processes that prepare the components for such coating and the coatings are needed.

SUMMARY

Disclosed are compositions comprising: a polyester macromer containing one or more chains of the residue of one or more diols and one or more diesters wherein the residue of the one or more diols and the one or more diesters alternate along the chain and a portion of the diesters are 1,1-diester-1-alkenes and at least one terminal end comprises the residue of one of the 1,1-diester-1 alkenes and wherein one or more terminal ends may comprise the residue of one or more diols. The composition may contain three or more alternating chains of the residue of one or more diols and one or more diesters, wherein at least some of the diesters are 1,1-diester-1-alkenes, wherein each of the chains are bonded at one end to an oxygen of the residue of a polyol having three or more of the oxygen atoms. The polyester macromers may correspond to Formula 1

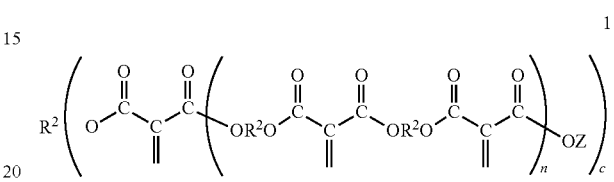

wherein Z is separately in each occurrence —$R^2OH$ or —$R^1$; $R^1$ is separately in each occurrence a hydrocarbyl group which may contain one or more heteroatoms; $R^2$ is separately in each occurrence a hydrocarbylene group having two or more bonds to oxygen atoms, wherein the hydrocarbylene group may contain one or more heteroatoms; c is an integer of 1 or more; and n is an integer of about 1 to 3. c may be an integer of about 3 to about 6.

The polyester macromers may contain one chain of the residue of one or more diols and one or more diesters, wherein at least some of the diesters are 1,1-diester-1-alkenes. These polyester macromers may correspond to Formula 2,

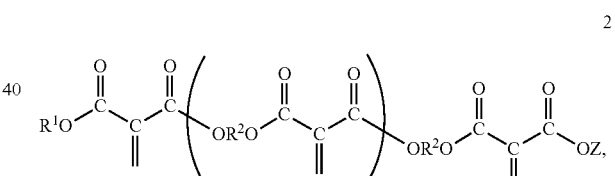

Z is separately in each occurrence —$R^2OH$ or —$R^1$; $R^1$ is separately in each occurrence a hydrocarbyl group which may contain one or more heteroatoms; $R^2$ is separately in each occurrence a hydrocarbylene group having two bonds to oxygen atoms, in the context of formula 2, wherein the hydrocarbylene group may contain one or more heteroatoms; and m is an integer of about 1 to 3. The polyester macromers disclosed may exhibit number average molecular weights of about 600 to about 3000.

The one or more diesters may comprise 1,1-diester-1-alkenes. In addition to the one or more 1,1-diester-1-alkenes, the one or more diesters may comprise one or more dihydrocarbyl dicarboxylates. The polyester macromers contain the residue of one or more 1,1-diester-1-alkenes and may contain the residue of one or more dihydrocarbyl dicarboxylates. The one or more dihydrocarbyl dicarboxylates may comprise one or more of aromatic dicarboxylates, aliphatic dicarboxylates and/or cycloaliphatic dicarboxylates. The polyester macromers containing the residue of one or more 1,1-diester-1-alkenes and the residue of one or more dihydrocarbyl dicarboxylates may correspond to one of Formula 3 to 6:

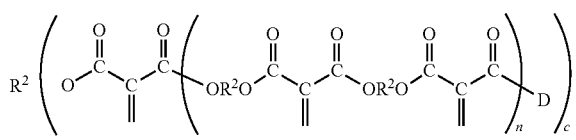

wherein D corresponds to the formula

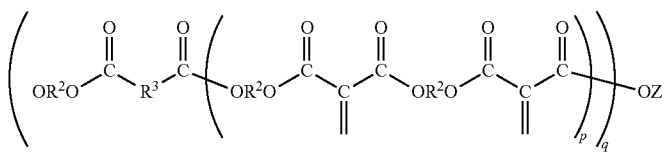

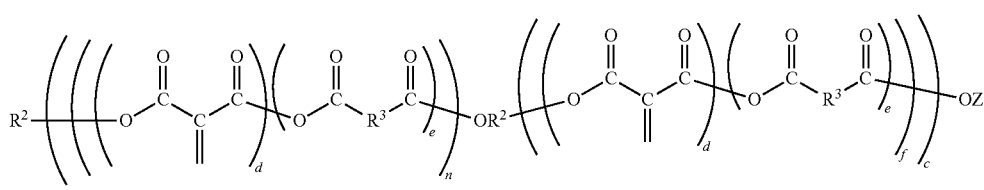

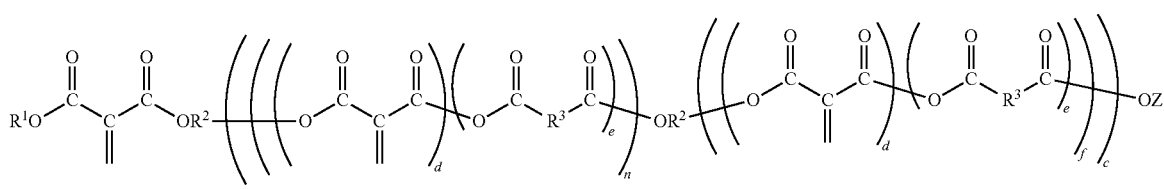

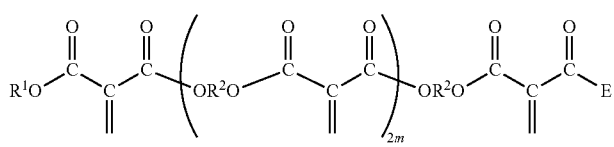

wherein Z; $R^1$; and $R^2$ are as previously described; $R^3$ is separately in each occurrence a hydrocarbylene group having two bonds to the carbonyl groups of the residue of the one or more diesters, wherein the hydrocarbylene group may contain one or more heteroatoms; c is an integer of 1 or more; d is an integer of 0 or 1; e is an integer of 0 or 1; f is the integer 1; m is an integer of 1 to 3; n is an integer of about 1 to 3; p is an integer of 2 or more; and q is an integer of 1 or more; wherein each pair of d and e must equal 1.

Disclosed is a composition comprising i) a plurality of polyester macromers as described herein; ii) one or more multifunctional monomers containing the residue of one or more polyols and one or more 1,1-diester-1-alkenes, wherein the multifunctional monomers have substantially all of the hydroxyl groups of the polyols replaced with the 1,1-diester-1-alkenes; and iii) one or more 1,1-diester-1-alkenes. The one or more polyols may be diols. The one or more multifunctional monomers may be difunctional monomers.

Disclosed is a composition comprising a) a composition comprising i) a plurality of polyester macromers as described herein; ii) one or more multifunctional monomers containing the residue of one or more polyols and one or more 1,1-diester-1-alkenes, wherein the multifunctional monomers have substantially all of the hydroxyl groups of the polyols replaced with the 1,1-diester-1-alkenes; and iii) one or more 1,1-diester-1-alkenes; b) a volatile solvent; c) optionally, an additional amount of one or more 1,1-diester-1-alkenes; d) one or more wetting agents; e) one or more UV stabilizers f) one or more additives to improve abrasion resistance and g) one or more additives to provide surface slip and anticratering properties. The solvent may be an alkoxy alkanol or an alkoxy alkyl acetate. The wetting agent may be a polyether modified polydimethyl siloxane. UV stabilizer may be a benzotriazole based or a hindered amine based compound. The composition may contain a scratch resistance additive which may be a nanometer sized silica filler. An additive to improve surface slip properties may be a polyester modified polydimethyl siloxane.

Disclosed is a composition comprising one or more polyester macromers and one or more of the polyols end-capped with one or more 1,1-diester-1-alkenes or multifunctional monomers, that is the terminal ends of the chains contain the residue of one or more 1,1-diester-1-alkenes and/or multifunctional monomers. The composition may contain a solvent. The one or more polyols may be one or more polyether polyols, polysiloxane polyols, polycarbonate polyols, polyester polyols, acrylic polyols or polybutadienyl polyols. The one or more polyols may be one or more polycarbonate polyols. The one or more polyols may be di or tri functional. The one or more polyols may have hydroxyl groups pendant from their backbone.

The compositions containing polyester macromers disclosed herein may fabricated into films or coatings. The coatings or films may have a thickness of about 0.001 micrometers or greater, or about 100 micrometers or greater. The coatings or films may have a thickness of about 160 micrometers or less or about 140 micrometers or less. Compositions containing a plurality of one or more polyester macromers disclosed herein may be cured. Compositions containing a plurality of one or more polyester macromers disclosed herein may be crosslinked after cure.

Disclosed is a composition comprising one or more polyester macromers as disclosed herein in one part and in a second part one or more compounds having basic character sufficient to initiate anionic polymerization of the polyester macromers; wherein when the two parts are combined the polyester macromers undergo curing. The one or more compounds having basic character may comprise one or more amines or polyamines. The one or more compounds having basic character may comprise one or more polyalkyleneimines.

Disclosed is an article having a coating containing one or more polyester macromers as part of the composition disposed on one or more of the surfaces or a portion of one or more surfaces of the article. The article may have a base coat upon which the polyester macromer composition is deposited. The base coat may contain pigments. The base coat may have a basic pH at the surface. The pigments may be basic. The polyester macromer coating may be clear.

Disclosed is a method comprising: contacting one or more polyols with an equivalents excess of one or more 1,1-diester 1-alkenes in the presence of a transesterification catalyst under conditions such that one or more multifunctional monomers are formed wherein the multifunctional monomers contain the one or more polyols having two or more of their hydroxyl groups replaced with the residue of the one or more 1,1-diester 1-alkenes; and, contacting the multifunctional monomers with an additional amount of the one or more polyols, with the proviso that the polyols are diols, or with one or more second polyols which are diols, in the presence of a transesterification catalyst under conditions such that one or more polyester macromers are prepared which contain one or more chains of the residue of one or more diols and one or more 1,1-diester-1-alkenes wherein the residue of the one or more diols and the one or more 1,1-diester-1 alkenes alternate along the chain and at least one terminal end comprises the residue of one of the 1,1-diester-1 alkenes and wherein one or more terminal ends may comprise the residue of one or more diols. Alternatively, the second step may comprise contacting the multifunctional monomers and an additional amount of the one or more polyols or with one or more second polyols with one or more compounds comprising one or more dihydrocarbyl dicarboxylates having the residue of a polyol bonded to each of the carbonyl groups such that one or more polyester macromers are prepared wherein at least some to the polyester macromers contain the residue of the one or more the dihydrocarbyl dicarboxylates in the one or more chains.

Disclosed is a method comprising: contacting one or more diols, one or more 1,1-diester 1-alkenes, and one or more dihydrocarbyl dicarboxylates in the presence of a transesterification catalyst under conditions that one or more polyester macromers are prepared which contain one or more chains of the residue of one or more diols, one or more dihydrocarbyl dicarboxylates and one or more 1,1-diester-1-alkenes wherein the residues of each are disposed in a random manner along the chain and at least one terminal end comprises the residue of one of the 1,1-diester-1 alkenes and wherein one or more terminal ends may comprise the residue of one or more diols.

Disclosed is a method comprising: contacting one or more polyols with an equivalents excess of one or more 1,1-diester 1-alkenes in the presence of a transesterification catalyst under conditions such that one or more multifunctional monomers are formed wherein the multifunctional monomers contain the one or more polyols having at least two of their hydroxyl groups replaced with the residue of the one or more 1,1-diester 1-alkenes; and contacting the one or more multifunctional monomers with one or more diols, one or more 1,1-diester 1-alkenes, and one or more dihydrocarbyl dicarboxylates in the presence of a transesterification catalyst under conditions that one or more polyester macromers are prepared which contain one or more chains of the residue of one or more diols, one or more dihydrocarbyl dicarboxylates and one or more 1,1-diester-1-alkenes wherein the residues of each are disposed in a random manner along the chain and at least one terminal end comprises the residue of one of the 1,1-diester-1 alkenes and wherein one or more terminal ends may comprise the residue of one or more diols.

Disclosed is a method comprising: contacting one or more multifunctional monomers which contain one or more polyols having their hydroxyl groups replaced with the residue of the one or more 1,1-diester 1-alkenes; one or more compounds comprising a dihydrocarbyl dicarboxylates having the residue of a polyol bonded to each of the carbonyl groups; and one or more polyols in the presence of a transesterification catalyst under conditions such that one or more polyester macromers are prepared which contain one or more chains of the residue of one or more polyols, one or more 1,1-diester-1-alkenes, and one or more compounds comprising a dihydrocarbyl dicarboxylates having the residue of a polyol bonded to each of the carbonyl groups and at least one terminal end comprises the residue of one of the 1,1-diester-1 alkenes and wherein one or more terminal ends may comprise the residue of one or more diols. The multifunctional monomers may be prepared by contacting one or more polyols with an equivalents excess of one or more 1,1-diester 1-alkenes in the presence of a transesterification catalyst under conditions such that one or more multifunctional monomers are formed. The one or more compounds comprising a dihydrocarbyl dicarboxylates having the residue of a polyol bonded to each of the carbonyl groups is prepared by contacting one or more diesters with an excess of one or more polyols in the presence of a transesterification catalyst under conditions such that one or more dihydrocarbyl dicarboxylates having the residue of a polyol bonded to each of the carbonyl groups is prepared.

In the transesterification process steps disclosed herein the one or more polyols or second polyols may be diols. The one or more dihydrocarbyl dicarboxylates may be one or more of aromatic dicarboxylates, aliphatic dicarboxylates and cycloaliphatic dicarboxylates. The one or more dihydrocarbyl dicarboxylates may be one or more malonates. The transesterification catalyst may be an acid, an ester of such acid or a lipase enzyme. The transesterification catalyst may be one or more acids having a pKa in a polar aprotic solvent of about −5 to about 14 or esters of the acids. The acid or the ester of the acid may be present in an amount of about 2.0 molar equivalents or less of the acid or the ester of acid per molar equivalent of the ester containing compounds transesterified. When the catalyst is an acid or an ester of an acid the method may be performed at a temperature of about 20° C. to about 160° C. The transesterification catalyst may be a lipase enzyme catalyst. When the catalyst is a lipase enzyme catalyst the transesterification step may be performed at an elevated temperature between about 20° C. and 70° C. During the disclosed methods volatile by-products may be formed and removed from the reaction mixture. The volatile by-products may be removed from the reaction mixture by applying a vacuum. The volatile by-products may be alcohols.

Disclosed is a method comprising contacting a composition containing one or more polyester macromers as disclosed herein with a surface of a substrate wherein the surface is at least mildly basic and forming a coating on the surface of the substrate comprising the composition containing the one or more polyester macromers. The substrate may be comprised of material that is at least mildly basic. A composition that contains a basic compound that initiates anionic polymerization for 1,1-disubstituted alkenes may be applied to the surface of the substrate before applying the composition containing one or more polyester macromers. Exemplary basic compounds comprise one or more amines, polyamine basic pigments; polyalkyleneamines, polyethylene imines and carboxylate salts. The methods for forming coatings may further comprise exposing the substrate with the composition containing one or more polyester macromers to a temperature of about 20° C. to about 150° C. for about 10 minutes to about 60 minutes under conditions such that the coating containing one or more polyester macromers disposed on the surface of the substrate is crosslinked. The coatings may also be cured with no heat input, at ambient temperatures, which requires greater cure times, or example up to about 24 hours.

The compositions containing polyester macromers can be used to prepare polyester compositions that can be cured and crosslinked using relatively mild conditions. The polyester macromers allow the tailoring of properties of polyester containing compositions. Specifically the polyester macromers allow the preparation of polyester compositions that have improved mechanical properties and elasticity. Coatings, films and fibers prepared from polyester compositions containing the polyester macromers exhibit enhanced properties including one or more of pencil hardness of greater than 7H, high gloss, solvent resistance, flexibility, excellent adhesion to base coats, metals, plastics, particles, and the like. The methods disclosed provide the ability to efficiently prepare the polyester macromers and compositions containing such macromers. The methods of preparing coatings and films allow the preparation of coatings and films with the above-described enhanced properties in an efficient manner.

DESCRIPTION OF FIGURES

FIG. 1 illustrates the results of gloss testing of a number of coatings.

FIG. 2 illustrates the results of solvent resistance testing of a number of coatings.

FIG. 3 illustrates the results of pencil hardness testing of a number of coatings.

DETAILED DESCRIPTION

The explanations and illustrations presented herein are intended to acquaint others skilled in the art with the invention, its principles, and its practical application. The specific embodiments of the present invention as set forth are not intended to be exhaustive or limiting of the invention. The scope of the invention should be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Unless defined otherwise, all technical and scientific terms used herein have the meaning commonly understood by a person skilled in the art. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Disclosed are compositions comprising polyester macromers containing in one or more chains the residue of one or more diols and one or more diesters wherein the residue of the one or more diols and the one or more diesters alternate along the chain and a portion of the diesters are 1,1-diester-1-alkenes and at least one terminal end comprises the residue of one of the 1,1-diester-1-alkenes and wherein one or more terminal ends may comprise the residue of one or more diols. The macromers may have two or greater of such chains. The chains may include the residue or one or more dihydrocarbyl dicarboxylates. The chains may contain the residue of one or more diols and one or more diesters wherein the diesters comprise one or more 1,1-diester-1-alkenes, the residue of the one or more diols and the one or more 1,1-diester-1 alkenes and optionally one or more dihydrocarbyl dicarboxylates may be randomly disposed along the chains. The polyester macromers may be used to form polyesters, blended with polyesters and/or other polymeric compounds to provide enhanced properties. Disclosed are methods of preparing the polyester macromers and incorporating them in a variety of polyester containing compositions. Disclosed are methods of preparing structures from polyester macromer containing compositions such as coatings, films, fibers, and particles.

As used herein, diester refers to any compound having two ester groups which can be subjected to transesterification. A 1,1-diester-1-alkene is a compound that contains two ester groups and a double bond bonded to a single carbon atom referred to as the one carbon atom. Dihydrocarbyl dicarboxylates are diesters having a hydrocarbylene group between the ester groups wherein a double bond is not bonded to a carbon atom which is bonded to two carbonyl groups of the diester.

The term "monofunctional" refers to the 1,1-diester-1-alkenes having only one core unit. The core unit comprises two carbonyl groups and a double bond bonded to a single carbon atom. The term "difunctional" refers to the 1,1-diester-1-alkenes having two core units (each including the reactive alkene functionality) bound through a hydrocarbylene linkage between one oxygen atom on each of two core formulas. The term "multifunctional" refers to the 1,1-diester-1-alkenes having two or more core units (each core unit including the reactive alkene functionality) bound together through a hydrocarbylene linkage between one oxygen atom on each of two or more core formulas.

Acid catalyst, as used herein, is an acidic species that catalyzes the transesterification reaction while minimizing or not contributing to side reactions. One or more as used herein means that at least one, or more than one, of the recited components may be used as disclosed. Nominal as used with respect to functionality refers to the theoretical functionality; generally this can be calculated from the stoichiometry of the ingredients used. Heteroatom refer to atoms that are not carbon or hydrogen such as nitrogen, oxygen, sulfur, and phosphorus; heteroatoms may include nitrogen and oxygen. Hydrocarbyl, as used herein, refers to a group containing one or more carbon atom backbones and hydrogen atoms, which may optionally contain one or more heteroatoms. Where the hydrocarbyl group contains heteroatoms, the heteroatoms may form one or more functional groups well-known to one skilled in the art. Hydrocarbyl groups may contain cycloaliphatic, aliphatic, aromatic, or any combination of such segments. The aliphatic segments can be straight or branched. The aliphatic and cycloaliphatic segments may include one or more double and/or triple bonds. Included in hydrocarbyl groups are alkyl, alkenyl, alkynyl, aryl, cycloalkyl, cycloalkenyl, alkaryl, and aralkyl groups. Cycloaliphatic groups may contain both cyclic portions and noncyclic portions. Hydrocarbylene means a hydrocarbyl group or any of the described subsets having more than one valence, such as alkylene, alkenylene, alkynylene, arylene, cycloalkylene, cycloalkenylene, alkarylene and aralkylene. Percent by weight or parts by weight refer to, or are based on, the weight or the compounds or compositions described unless otherwise specified. Unless otherwise stated parts by weight are based 100 parts of the composition.

The term "ketal" refers to a molecule having a ketal functionality; i.e., a molecule containing a carbon bonded to two —OR groups, where O is oxygen and R represents any alkyl group or hydrogen. The terms "volatile" refers to compounds which are capable of evaporating readily at normal temperatures and pressures. "Non-volatile" refers to compounds which are not capable of evaporating readily at normal temperatures and pressures. The term "stabilized" (e.g., in the context of "stabilized" 1,1-diester-1-alkenes, or compositions comprising the same, refers to the tendency of the compounds (or their compositions) to substantially not polymerize with time, to substantially not harden, form a gel, thicken, or otherwise increase in viscosity with time, and/or to substantially show minimal loss in cure speed (i.e., cure speed is maintained) with time. Residue with respect to an ingredient used to prepare the polyester macromers disclosed herein means that portion of the ingredient, such as a polyol, such as a diol, a diester, such as a 1,1-diester-1-alkene and/or a dihydrocarbyl dicarboxylate, that remains in the compound after inclusion as a result of the methods disclosed herein. Substantially all as used herein that greater than 95 percent of the referenced parameter, composition or compound meet the defined criteria, greater than 99 percent of the referenced parameter, composition or compound meet the defined criteria, or greater than 99.5 percent of the referenced parameter, composition or compound meet the defined criteria.

Disclosed are polyester macromers which contain one or more chains containing the residue of one or more diols and one or more diesters wherein a portion of the diesters comprise 1,1-diester-1-alkenes. The residue of the diols and the diesters can alternate along the chains or can be disposed randomly along the chains. The diesters may further comprise any diester compound that will undergo transesterification with a polyol or diol. Among diester compounds are dihydrocarbyl dicarboxylates. The polyester macromers may have three or more chains as described. The polyester macromers having three or more chains contain the residue of a polyol originally having three or greater hydroxyl groups. The three or more chains propagate from each of the three or more hydroxyl groups. The polyols having three or more chains function as initiators from which each of the chains of the polyester macromers propagate. If the polyol is a diol a single chain is produced because the macromer formed is linear. Where a polyol having three or more hydroxyls is used to prepare the macromer, it may have two or more chains as not all of the hydroxyls may propagate chains. The macromers may contain one or more chains, may contain two or more chains, or may contain three or more chains. The macromers may contain eight or less chains, six or less chains, four or less chains or three or less chains. The chains may comprise the residue of one or more polyols, one or more diols and one or more diesters, including one or more 1,1-diester-1-alkenes and optionally one or more dihydrocarbyl dicarboxylates. The chains may comprise the residue of one or more diols and one or more diesters, including one or more 1,1-diester-1-alkenes and optionally one or more dihydrocarbyl dicarboxylates. The polyester macromers contain the residue of at least one 1,1-diester-1-alkenes at the terminal end of one of the chains. The polyester macromers may further comprise one or more diols or dihydrocarbyl dicarboxylates at the terminal end of one or more of the chains. Substantially all of the terminal ends of chains may be 1,1-diester-substituted alkenes.

The polyester macromers may comprise sufficient amount of the residue of one or more polyols, in this context the polyols have 3 or greater hydroxyl groups, to initiate the desired number of chains. The residue of the polyols in the polyester macromers may be about 20 mole percent or greater; about 30 mole percent or greater or about 40 mole percent or greater. The residue of the polyols in the polyester macromers may be about 50 mole percent or less; or about 40 mole percent or less. The polyester macromers may comprise sufficient amount of the residue of one or more diols, in this context the polyols have 2 hydroxyl groups, to prepare polyester macromers having the desired chain length and number average molecular weight. The residue of the diols in the polyester macromers may be about 20 mole percent or greater; about 40 mole percent or greater or about 50 mole percent or greater. The residue of the diols in the polyester macromers may be about 50 mole percent or less; about 40 mole percent or less or about 30 mole percent or less. The polyester macromers may comprise sufficient amount of the residue of the 1,1-diester-substituted-1-alkenes to provide the desired crosslink density to compositions containing the polyester macromers. The residue of the 1,1-diester-substituted-1-alkenes in the poly-ester macromers may be about 20 mole percent or greater; about 30 mole percent or greater or about 40 mole percent or greater. The residue of the 1,1-diester-substituted-1-alkenes in the polyester macromers may be about 50 mole percent or less; about 40 mole percent or less or about 30 mole percent or less. The polyester macromers may comprise suffi-cient amount of the residue of the dihydrocarbyl dicarboxylates to provide the desired space between crosslinks to compositions containing the polyester macromers to provide the desired flexibility and/or elasticity to the structures containing the polyester macromers. The residue of the dihydrocarbyl dicarboxylates in the polyester macromers may be about 10 mole percent or greater; about 20 mole percent or greater or about 30 mole percent or greater. The residue of the dihydrocarbyl dicarboxylates in the polyester macromers may be about 50 mole percent or less; about 40 mole percent or less or about 30 mole percent or less.

The polyester macromers may correspond to Formula 1

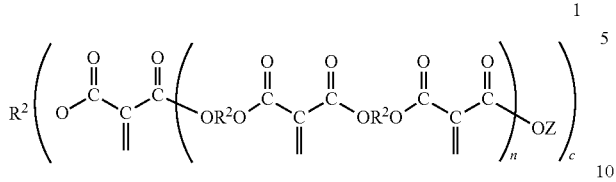

wherein Z is separately in each occurrence —$R^2$OH or —$R^1$; $R^1$ is separately in each occurrence a hydrocarbyl group which may contain one or more heteroatoms; $R^2$ is

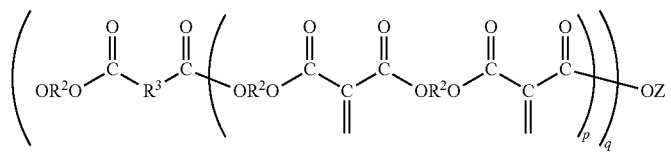

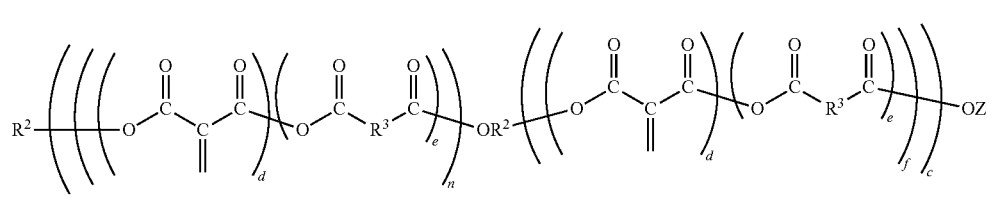

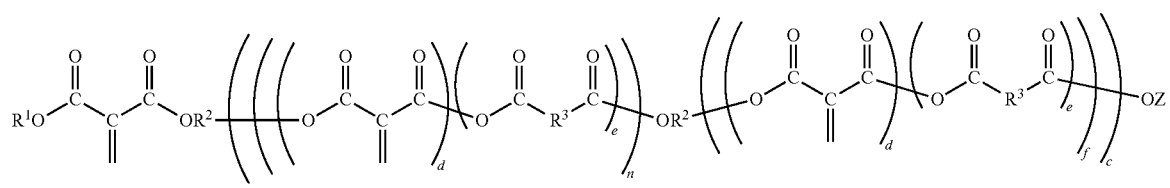

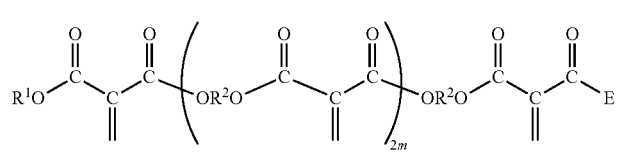

separately in each occurrence a hydrocarbylene group having two or more bonds to oxygen atoms; c is an integer of 1 or more; and n is an integer of about 1 to 3. With respect to $R^2$ the bonds to oxygen atoms may include bonds to the oxygen of a polyol, a diol, or a diester or the residue thereof depending on the context of use of $R^2$.

The polyester macromers may contain one chain of the residue of one or more diols and one or more diesters. The polyester macromers may correspond to Formula 2,

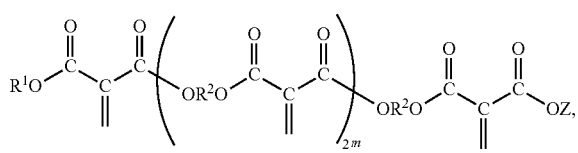

wherein Z, $R^1$ and $R^2$ are as previously defined; and m is an integer of about 1 to 3.

The polyester macromers containing the residue of one or more 1,1-diester-1-alkenes and the residue of one or more dihydrocarbyl dicarboxylates may correspond to one of Formulas 3 to 6:

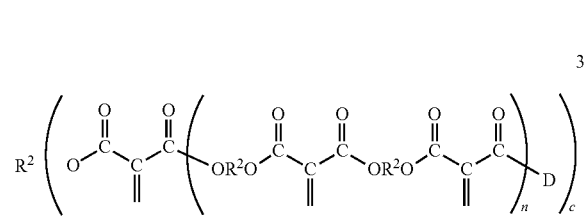

wherein D corresponds to the formula

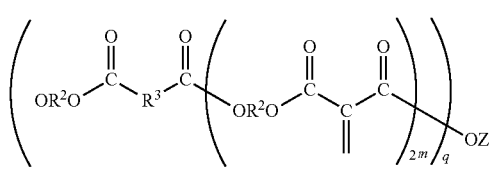

wherein E corresponds to the formula,

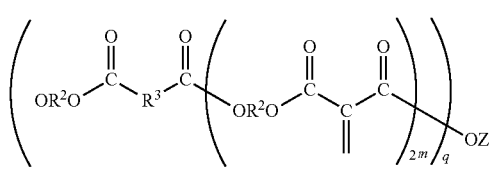

wherein Z, $R^1$, $R^2$ and m are as previously defined; $R^3$ is separately in each occurrence a hydrocarbylene group having two bonds to the carbonyl groups of one or more of the diesters or to the residue of such diesters depending on the context, wherein the hydrocarbylene group may contain one or more heteroatoms; c is an integer of 1, or 2 or more; d is an integer of 0 or 1; e is an integer of 0 or 1; f is the integer 1; n is an integer of about 1 to 3; p is an integer of 2 or more; and q is an integer of 1 or more; wherein each pair of d and e must equal 1. p may be an integer of 3 or greater. p may be an integer of 8 or less, 6 or less or 3 less. q may be an integer of 4 or less or 3 or less.

The polyester macromers may contain in their backbone repeating units comprising the residue of at least one diester and one diol. A significant portion of the diesters are 1,1-diestersubstituted-1-alkenes. A portion of the diesters may be 1,1-dihydrocarbyl dicarboxylates. The backbone of polyester macromers contain a sufficient number of repeating units comprising the residue of at least one diester and one diol to facilitate the use of the polyester macromers as disclosed herein such as in coatings, films, fibers, particles and the like. The number of repeating units comprising the residue of at least one diester and one diol in polyester macromers may be 2 or greater, 4 or greater or 6 or greater. The number of repeating units comprising the residue of at least one diester and one diol in polyester macromers may be 10 or less, 8 or less, or 6 or less. The diesters in some polyester macromers can be all 1,1-diester-1-alkenes. The diesters in some polyester macromers can be 1,1-diester-1-alkenes and dihydrocarbyl dicarboxylates. The ratio of 1,1-diester-1-alkenes and dihydrocarbyl dicarboxylates in some polyester macromers is selected to provide the desired degree of crosslinking in structures prepared from the polyester macromers. The ratio of 1,1-diester-1-alkenes and dihydrocarbyl dicarboxylates in some polyester macromers may be 1:1 or greater, 6:1 or greater or 10:1 or greater. The ratio of 1,1-diestersubstituted-1-alkenes and dihydrocarbyl dicarboxylates in some polyester macromers may be 15:1 or less, 10:1 or less, 6:1 or less or 4:1 or less. The polyester macromers may exhibit a number average molecular weight of about 600 or greater, about 900 or greater, about 1000 or greater or about 1200 or greater. The polyester macromers may exhibit a number average molecular weight of about 3000 or less, about 2000 or less or about 1600 or less. Number average molecular weight as used herein is determined dividing total weight of all the polymer molecules in a sample, by the total number of polymer molecules in a sample. The polydispersity of the polyester macromers may be about 1.05 or greater or about 1.5 or greater. The polydispersity of the polyester macromers may be about 2.5 or less or about 1.5 or less. For calculating the polydispersity the weight average molecular weight is determined using gel permeation chromatography using a polymethylmethacrylate standard.

The polyester macromers disclosed may be prepared from 1,1-diester-1-alkenes, diols, polyols and/or dihydrocarbyl dicarboxylates. The choice of specific ingredients, ratios of ingredients and sequence of process steps impact the final structure and content of the polyester macromers. The presence of polyols having greater than two hydroxyl groups function to initiate the chains results in the formation of polyester macromer having more than two chains, that is the macromer exhibits branching and the polymer is not linear. The 1,1-diester-1-alkenes help form the chains and introduce pendant alkene groups capable of crosslinking via anionic and/or free radical polymerization. The diols may initiate a single chain and chain extend the polyester macromers. The dihydrocarbyl dicarboxylates help form the chains and function to space the pendant alkene groups from one another, thereby increasing the distance between crosslinks and the average molecular weight per crosslink.

The 1,1-diester-1-alkenes comprise a central carbon atom referred to as the 1 carbon atom. Bonded to the 1 carbon atom are the carbonyl groups of two ester groups and another carbon atom via a double bond. The double bond, due to it being bonded to two carbonyl groups, is highly reactive. The doubly bonded carbons may be part of an alkenyl group which is highly reactive. The alkenyl group may be a $C_{2-4}$ alkenyl group, or a methylene group (C=C).

The esters contain hydrocarbyl groups bonded to the oxygen bonded to the carbonyl group wherein the hydrocarbyl groups may contain one or more heteroatoms, including heteroatom containing functional groups. The hydrocarbyl groups can be any hydrocarbyl groups that can undergo transesterification under the conditions disclosed herein. The hydrocarbyl groups on the ester may be separately in each occurrence alkyl, alkenyl, cycloalkyl, heterocyclyl, alkyl heterocyclyl, aryl, aralkyl, alkaryl, heteroaryl, or alkheteroaryl, or polyoxyalkylene, or both of the hydrocarbyl groups may form a 5-7 membered cyclic or heterocyclic ring. The hydrocarbyl groups on the ester may be separately in each occurrence $C_1$-$C_{15}$ alkyl, $C_2$-$C_{15}$ alkenyl, $C_3$-$C_9$ cycloalkyl, $C_{2-20}$ heterocyclyl, $C_{3-20}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene, or both of the hydrocarbyl groups form a 5-7 membered cyclic or heterocyclic ring. The recited groups may be substituted with one or more substituents, which do not interfere with the transesterification reaction. Exemplary substituents include halo, alkylthio, alkoxy, hydroxyl, nitro, azido, cyano, acyloxy, carboxy, or ester. The hydrocarbyl groups on the ester may be separately in each occurrence $C_1$-$C_{15}$ alkyl, $C_3$-$C_6$ cycloalkyl, $C_{4-18}$ heterocyclyl, $C_{4-18}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene. The hydrocarbyl groups on the ester may be separately in each occurrence a $C_{1-4}$ alkyl. The hydrocarbyl groups on the ester may be separately in each occurrence methyl or ethyl. The hydrocarbyl groups on the ester may be the same for each ester group on the 1,1-di-1-alkene compounds. Exemplary compounds are dimethyl, diethyl, ethylmethyl, dipropyl, dibutyl, diphenyl, and ethyl-ethylgluconate malonates. The compounds may be dimethyl and diethyl methylene malonate. The 1,1-diester-1-alkenes can be prepared as disclosed in Malofsky et al., U.S. Pat. Nos. 8,609,885 and 8,884,051; and Malofsky et al. U.S. Pat. No. 9,108,914.

The 1,1-diester-1-alkene compounds may correspond to formula 7:

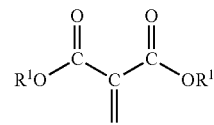

7

$R^1$ is separately in each occurrence a group that can undergo replacement or transesterification under the conditions of the methods disclosed herein. $R^1$ may be separately in each occurrence alkyl, alkenyl, cycloalkyl, heterocyclyl, alkyl heterocyclyl, aryl, aralkyl, alkaryl, heteroaryl, or alkheteroaryl, or polyoxyalkylene, or both of the $R^1$s form a 5-7 membered cyclic or heterocyclic ring. $R^1$ may be separately in each occurrence $C_1$-$C_{15}$ alkyl, $C_2$-$C_{15}$ alkenyl, $C_3$-$C_9$ cycloalkyl, $C_{2-20}$ heterocyclyl, $C_{3-20}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene, or both of the $R_1$ groups form a 5-7 membered cyclic or heterocyclic ring. The recited groups may be substituted with one or more substituents, which do not interfere with the transesterification reaction. Exemplary substituents include halo alkylthio, alkoxy, hydroxyl, nitro, azido, cyano, acyloxy, carboxy, or ester. $R^1$ may be separately in each occurrence $C_1$-$C_{15}$ alkyl, $C_3$-$C_6$ cycloalkyl, $C_{4-18}$ heterocyclyl, $C_{4-18}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene. $R^1$ may be separately in each occurrence a $C_{1-4}$ alkyl. $R^1$ may be separately in each occurrence methyl or ethyl. $R^1$ may be the same or different for each ester group on the 1,1-disubstituted alkene compounds.

A preferred class of 1,1-disubstituted alkene compounds are the methylene malonates which may correspond to formula 8:

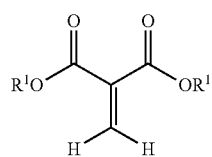

8 wherein $R^1$ is as described herein before.

The 1,1-diester-alkenes may be prepared using a method which results in a sufficiently high purity so that they can be included into polyester macromers that can be polymerized and/or crosslinked. The purity of the 1,1-diester-1-alkenes may be sufficiently high so that 70 mole percent or more, 80 mole percent or more, 90 mole percent or more, 95 mole percent or more, or 99 mole percent or more of the polyester macromers containing 1,1-diester-1-alkenes may be converted to polymer during a polymerization or curing process. The purity of the 1,1-diester-1-alkenes may be about 85 mole percent or more, about 90 mole percent or more, about 93 mole percent or more, about 95 mole percent or more, about 97 mole percent or more, or about 99 mole percent or more, based on the total moles of the 1,1-diester-1-alkenes. If the 1,1-diester-1-alkenes includes the analogous 1,1-diester alkane it may be about 10 mole percent or less, or about 1 mole percent or less. The concentration of any impurities containing a dioxane group may be about 2 mole percent or less, about 1 mole percent or less, about 0.2 mole percent or less, or about 0.05 mole percent or less, based on the total moles of the 1,1-diester1-1-alkenes. The total concentration of any impurity having the alkene group replaced by an analogous hydroxyalkyl group (e.g., by a Michael addition of the alkene with water) may be about 3 mole percent or less, about 1 mole percent or less, about 0.1 mole percent or less, or about 0.01 mole percent or less, based on the total moles in the 1,1-diester-1-alkenes. The 1,1-diester-1-alkenes may be prepared by a process including one or more (e.g., two or more) steps of distilling a reaction product or an intermediate reaction product (e.g., a reaction product or intermediate reaction product of a source of formaldehyde and a malonic acid ester).

Polyols useful are compounds having a hydrocarbylene backbone with two or more hydroxyl groups bonded to the hydrocarbylene backbone and which may capable of transesterifying ester compounds under the transesterification conditions disclosed herein. Polyols useful herein fall in two groups. The first group are diols which have two hydroxyl groups bonded to a hydrocarbylene backbone and which function both to initiate and extend the chains of the polyester macromers. Polyols with greater than two hydroxyl groups bonded to the hydrocarbylene backbone function to initiate more than two chains. Diols may also function to extend the more than two chains. The polyols may have from 2 to 10 hydroxyl groups, from 2 to 4 hydroxyl groups or from 2 to 3 hydroxyl groups. The backbone for the polyols, including diols, may be alkylene, alkenylene, cycloalkylene, heterocyclylene, alkyl heterocyclylene, arylene, aralkylene, alkarylene, heteroarylene, alkheteroarylene, or polyoxyalkylene. The backbone may be $C_1$-$C_{15}$ alkylene, $C_2$-$C_{15}$ alkenylene, $C_3$-$C_9$ cycloalkylene, $C_{2-20}$ heterocyclylene, $C_{3-20}$ alkheterocyclylene, $C_{6-18}$ arylene, $C_{7-25}$ alkarylene, $C_{7-25}$ aralkylene, $C_{5-18}$ heteroarylene, $C_{6-25}$ alkyl heteroarylene or polyoxyalkylene. The alkylene sections may be straight or branched. The recited groups may be substituted with one or more substituents which do not interfere with the transesterification reaction. Exemplary substituents include halo alkylthio, alkoxy, hydroxyl, nitro, azido, cyano, acyloxy, carboxy, or ester. The backbone may be $C_{2-10}$ alkylene groups. The backbone may be a $C_{2-8}$ alkylene group, which may be straight or branched, such as ethylene, propylene, butylene, pentylene, hexylene, 2-ethyl hexylene, heptylene, 2-methyl 1,3 propylene or octylene. The diols having a methyl group at the 2 position of an alkylene chain may be used. Exemplary diols include ethane diol, propane diol, butane diol, pentane diol, hexane diol, 2 ethyl hexane diol, heptane diol, octane diol, 2-methyl 1,3 propylene glycol, neopentyl glycol and 1,4-cyclohexanol. The polyol may correspond to formula 9

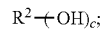

the diol may correspond to formula 10: HO—$R^2$—OH;
wherein $R^2$ is separately in each occurrence a hydrocarbylene group having two or more bonds to the hydroxyl groups of a polyol. $R^2$ may be separately in each occurrence alkylene, alkenylene, cycloalkylene, heterocyclylene, alkyl heterocyclylene, arylene, aralkylene, alkarylene, heteroarylene, alkheteroarylene, or polyoxyalkylene. $R^2$ may be separately in each occurrence $C_1$-$C_{15}$ alkylene, $C_2$-$C_{15}$ alkenylene, $C_3$-$C_9$ cycloalkylene, $C_{2-20}$ heterocyclylene, $C_{3-20}$ alkheterocyclylene, $C_{6-18}$ arylene, $C_{7-25}$ alkarylene, $C_{7-25}$ aralkylene, $C_{5-18}$ heteroarylene, $C_{6-25}$ alkyl heteroarylene or polyoxyalkylene. The recited groups may be substituted with one or more substituents which do not interfere with the transesterification reaction. Exemplary substituents include halo, alkylthio, alkoxy, hydroxyl, nitro, azido, cyano, acyloxy, carboxy, or ester. $R^2$ may be separately in each occurrence a $C_{2-8}$ alkylene group, such as ethylene, propylene, butylene, pentylene, hexylene, 2-ethyl hexylene, heptylene, 2-methyl 1,3 propylene or octylene. Exemplary $C_3$-$C_9$ cycloalkylenes include cyclohexylene. The alkylene groups may be branched or straight and may have a methyl group on the 2 carbon. Among preferred alkarylene polyols are polyols with the structure of -aryl-alkyl-aryl- (such as -phenyl-methyl-phenyl- or -phenyl-propyl-phenyl-) and the like. Among preferred alkyl cycloalkylene poly-yls are those with the structure of -cycloalkyl-alkyl-cycloalkyl- (such as -cyclohexyl-methyl-cyclohexyl- or -cyclohexyl-propyl-cyclohexyl-) and the like. c may be an integer of 8 or less, 6 or less, 4 or less, or 3 or less and c may be an integer of 1 or greater, 2 greater or 3 or greater.

The one or more dihydrocarbyl dicarboxylates are compounds with two ester groups having a hydrocarbylene group disposed between the ester groups. The one or more dihydrocarbyl dicarboxylates comprise one or more of aromatic dicarboxylates, aliphatic dicarboxylates and cycloaliphatic dicarboxylates or may be one or more dihydrocarbyl dicarboxylates wherein one of the hydrocarbyl groups is aliphatic, cycloaliphatic or aromatic and the other is selected from another class of aliphatic, cycloaliphatic or aromatic. The one or more dihydrocarbyl dicarboxylates comprise one or more of aromatic dicarboxylates having 8 to 14 carbon atoms in the backbone, aliphatic dicarboxylates having 1 to 12 carbon atoms in the backbone and cycloaliphatic dicarboxylates having 8 to 12 carbon atoms in the backbone. The one or more dihydrocarbyl dicarboxylates comprise one or more malonates, terephthalates, phthalates, isophthalates, naphthalene-2,6-dicarboxylates, 1,3-phenylenedioxy diacetates, cyclohexane-dicarboxylates, cyclohexanediacetates, diphenyl-4,4'-dicarboxylates, succinates, glutarates, adipates, azelates, sebacates, or mixtures thereof. The one or more dihydrocarbyl dicarboxylates may comprise one or more malonates. The one or more dihydrocarbyl dicarboxylates correspond to the formula 11:

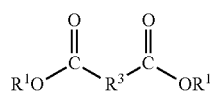

wherein $R^1$ is as previously described; and
$R^3$ is separately in each occurrence a hydrocarbylene group having two bonds to the carbonyl groups of the diester wherein the hydrocarbylene group may contain one or more heteroatoms. $R^3$ may be separately in each occurrence arylene, cycloalkylene, alkylene or alkenylene. $R^3$ may be separately in each occurrence $C_{8-14}$ arylene, $C_{8-12}$ cycloalkylene, $C_{1-12}$ alkylene or $C_{2-12}$ alkenylene. $R^3$ may be methylene.

Some of the methods for the preparation of the polyester macromers involve the preparation of intermediate compounds. One class of intermediate compounds is the multifunctional monomers. The multifunctional monomers may be prepared from 1,1-diester-1-alkenes and polyols, including diols. Where the polyol has greater than two hydroxyl groups, preparation of a multifunctional monomer is desired before chain extension. Multifunctional monomers comprise a polyol wherein at least two of the hydroxyl groups are replaced by the residue of 1,1-diester-1-alkenes. Where there are greater than two hydroxyl groups on the polyol it is possible that not all of the hydroxyl groups react with 1,1-diester-1-alkenes. It is desirable to react substantially all of the hydroxyl groups with the 1,1-diester-1-alkenes. The alternatives discussed hereinbefore for the polyols and 1,1-diester-1-alkenes as far as structure are also applicable to the multifunctional monomers. Where a polyol with 3 or greater hydroxyl groups are used to prepare the multifunctional monomers they correspond to formula 12

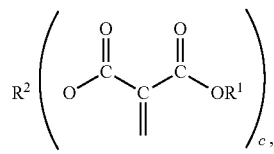

and
where diols used to initiate the multifunctional monomers they correspond to formula 13;

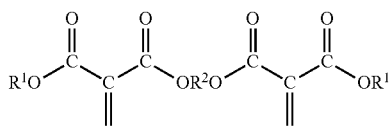

wherein $R^1$, $R^2$ and c are as defined hereinbefore. The multifunctional monomers can be prepared as disclosed hereinafter and as disclosed in Malofsky US 2014/0329980 and in commonly owned patent application Ser. No. 14/814,961 filed on Jul. 31, 2015.

Another intermediate which may be used in the preparation of polyester macromers is one or more compounds comprising the one or more dihydrocarbyl dicarboxylates having the residue of a polyol, such as a diol, bonded to each of the carbonyl groups. These compounds may be referred to a polyol capped dihydrocarbyl dicarboxylates. Some of them may be called diol capped dihydrocarbyl dicarboxylates. Each ester group of the dihydrocarbyl dicarboxylates is subjected to transesterification to replace the hydrocarbyl groups with polyols, such as diols. The resulting polyol capped dihydrocarbyl dicarboxylates have terminal hydroxyl groups. The polyol capped dihydrocarbyl dicarboxylates may correspond to formula 14;

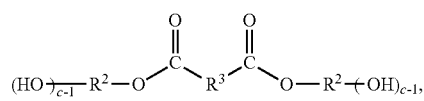

and
the diol capped dihydrocarbyl dicarboxylates may correspond to formula 15;

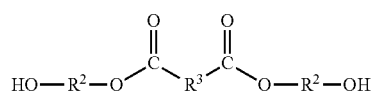

wherein $R^2$, $R^3$ and c are as described hereinbefore. In this context the hydrocarbylene of $R^3$ is bonded to the carbonyl groups of the residue of a diester in the polyol capped dihydrocarbyl dicarboxylates.

The polyester macromers may be used in compositions that are useful in preparing polymers and structures from the polymers. The compositions may be assembled by blending the polyester macromers with desired components. The compositions may comprise or include mixtures of compounds formed in the preparation of the polyester macromers. Other ingredients may be added to the mixtures of compounds formed in the preparation of the polyester macromers to form compositions which are designed to be used in the preparation of polymers containing the polyester macromers or structures formed from the polymers or polyester macromers. One composition comprises i) a plurality of polyester macromers disclosed herein; ii) one or more multifunctional monomers containing the residue of one or more polyols and one or more 1,1-diester-1-alkenes, wherein the multifunctional monomers have substantially all of the hydroxyl groups of the polyols replaced with the 1,1-diester-1-alkenes; and iii) one or more 1,1-diester-1-alkenes. Each of these ingredients are disclosed hereinbefore. This composition can be taken from the reaction mixture formed when the polyester macromers are prepared. The resulting reaction mixture can be subjected to a separation process, such as distillation to remove an excess one or more of the more volatile species, such as alcohols, polyols or unreacted dihydrocarbyl dicarboxylates, to achieve the desired concentrations of components. One or more of the recited compounds may be added to achieve the desired component concentrations. Plurality with respect to the polyester macromers mean that a number of polyester macromer units which may be the same or different polyester macromers are present. The polyester macromers are present in sufficient amount to prepare the desired polymers and structures from the polymers and introduce a desired level of crosslinking. Any one or more of the polyester macromers disclosed herein may be used in the compositions. Polyester macromers containing the residue of one or more dihydrocarbyl dicarboxylates in the backbone may be utilized. Polyester macromers used in the compositions may comprise the residue of one or more polyols and one or more 1,1-diester-1-alkenes. The 1,1-diester-1-alkenes are present to function as a reactive diluent and to facilitate forming a composition that exhibits a target viscosity. The 1,1-diester-1-alkenes may provide rapid reactivity of the polymer or structures prepared. The one or more multifunctional monomers are present to enhance crosslinking of the polymer or structures prepared. The components are present in sufficient amounts to achieve their recited purpose. The plurality of polyester macromers are present in an amount of about 10 percent by weight or greater of the composition, about 30 percent by weight or greater or about 60 percent by weight or greater. The plurality of polyester macromers are present in an amount of about 80 percent by weight or less of the composition, about 70 percent by weight or less or about 40 percent by weight or less. The multifunctional monomers are present in an amount of about 5 percent by weight or greater of the composition, about 10 percent by weight or greater, about 20 percent by weight or greater, or about 30 percent by weight or greater. The multifunctional monomers are present in an amount of about 40 percent by weight or less of the composition, about 30 percent by weight or less or about 20 percent by weight or less. The 1,1-diester-1-alkenes are present in an amount of about 0 percent by weight or greater of the composition, about 1 percent by weight or greater, about 5 percent by weight or greater, about 10 percent by weight or greater or about 20 percent by weight or greater. The 1,1-diester-1-alkenes are present in an amount of about 40 percent by weight or less of the composition, about 30 percent by weight or less or about 20 percent by weight or less. The one or more polyols may be diols. The multifunctional monomer may be difunctional.

The composition comprising i) a plurality of polyester macromers disclosed herein; ii) one or more multifunctional monomers containing the residue of one or more polyols and one or more 1,1-diester-1-alkenes, wherein the multifunctional monomers have substantially all of the hydroxyl groups of the polyols replaced with the 1,1-diester-1-alkenes; and iii) one or more 1,1-diester-1-alkenes may be used as the basis for preparing additional compositions. This composition may be used in such other compositions in sufficient amount to function as desired. This composition may be present in an amount of about 30 percent by weight or greater of the formed composition, about 60 percent by weight or greater or about 80 percent by weight or greater. This composition may present in an amount of about 80 percent by weight or less of the composition, about 60 percent by weight or less or about 30 percent by weight or less. Such compositions may contain a volatile solvent. The volatile solvent may be any solvent that does not react with the components or interfere in the curing of the compositions. The solvents may be volatile at about 50° C. or greater. The solvent may be volatile polar solvents. Included in such solvents are alkoxy alkanols, acetate capped glycol ethers having no hydroxyl groups and the like. Exemplary acetate capped glycol ethers having no hydroxyl groups include alkylene glycols having terminal alkoxy groups and acetate groups. The alkylene glycols may be based on ethylene, propylene and/or butylene glycols. The alkoxy groups may be $C_{1-10}$ alkoxy groups such as methoxy, ethoxy, propoxy and butoxy groups. Exemplary solvents include 2-butoxy ethanol and propylene glycol methyl ether acetate. The volatile solvents are present in sufficient amount to facilitate use of the compositions as desired that is the solvents facilitate delivery of the compositions. The volatile solvents are present in an amount of about 0 percent by weight or greater of the composition, about 5 percent by weight or greater, about 10 percent by weight or greater or about 20 percent by weight or greater. The volatile solvents are present in an amount of about 40 percent by weight or less of the composition, about 20 percent by weight or less or about 10 percent by weight or less. The compositions formed may contain an additional amount of 1,1-diester-1-alkenes. The additional 1,1-diester-1-alkenes are present in the compositions formed to function as reactive diluents and to accelerate polymerization. The additional 1,1-diester-1-alkenes may be present in an amount of about 5 percent by weight or greater of the composition, about 10 percent by weight or greater or about 30 percent by weight or greater. The additional 1,1-diester-1-alkenes may be present in an amount of about 50 percent by weight or less of the composition, about 40 percent by weight or less or about 30 percent by weight or less. The formed compositions may further contain one or more wetting or levelling agents which facilitate the application of such compositions to substrates. Any wetting and or levelling agent which enhances the application of the compositions to a substrate may be used. Exemplary classes of wetting or levelling agents include polyether modified polydimethyl siloxanes, fluorinated hydrocarbons and the like. The wetting agents may be polyether modified polydimethyl siloxanes. The wetting and/or levelling agents are present in sufficient amount to facilitate application of the compositions to a substrates surface. The wetting agents may be present in an amount of about 0.01 percent by weight or greater of the composition, about 0.5 percent by weight or greater or about 5 percent by weight or greater. The wetting agents may be present in an amount of about 5 percent by weight or less of the composition, about 2 percent by weight or less or about 1 percent by weight or less. The formed compositions may further contain one or more UV stabilizers which inhibit the degradation of structures containing the polyester macromers. Any UV stabilizer which inhibits degradation due to exposure to UV rays may be used. Exemplary classes of ultraviolet light stabilizers include benzophenones, benzotriazoles and hindered amines (commonly known as hindered amine light stabilizers (HALS). Exemplary UV light stabilizers include Cyasorb UV-531 2-hydroxy-4-n-octoxy-benzophenone, Tinuvin 571 2-(2H-benzotriazol-2-yl)-6-dodecyl-4-methylphenol, branched and linear Tinuvin 1,2,3 bis-(1-octyloxy-2,2,6,6, tetramethyl-4-piperidinyl) sebacate and Tinuvin 765, bis(1,2,2,6,6,-pentamethyl-4-piperidinyl) sebacate. The UV light stabilizers are present in sufficient amount to enhance durability of the compositions containing polyester macromers. The UV light stabilizers may be present in an amount of about 0.01 percent by weight or greater of the composition, about 0.1 percent by weight or greater or about 0.2 percent by weight or greater. The UV light stabilizers may be present in an amount of about 5 percent by weight or less of the composition, about 3 percent by weight or less, about 2 percent by weight or less or about 1 percent by weight or less. The composition may further comprise defoamers and/or deaerators. The compositions containing polyester macromers may foam during processing which can cause problems with respect to surface and appearance of the coating. Any defoamer and/or deaerator which prevents foaming or the formation of bubbles and which does not negatively impact the properties of the composition may be used. Exemplary defoamers are silicone defoamers, silicone free defoamers, polyacrylate defoamers, mixtures thereof and the like. Exemplary defoamers include FOAM BLAST™ 20F, FOAM BLAST™ 30 silicone defoaming compounds and FOAM BLAST™550 polyacrylate defoamers available from Emerald; TEGO AIREX™ 920 polyacrylate defoamer and TEGO AIREX™ 980 from Degussa, SILMER ACR™ Di-10 and ACR™ Mo-8 polydimethylsiloxane acrylate copolymer from Siltech Corporation, FOAMEX N™ or TEGO AIREX™ 900 silicone based defoamers available from Degussa or BYK™ 1790 silicone-free defoamer from BYK Chemie. The defoamer/deaerator is present in the polyester macromer compositions in a sufficient amount to prevent formation of bubbles and/or foam. If too much is used, adhesion to the desired surfaces and adhesives may be negatively impacted. The defoamer and/or deaerator may be present in an amount of about 0.05 percent by weight or greater based on the weight of the composition and more preferably about 0.1 percent by weight or greater. The defoamer/deaerator may be present in an amount of about 2.0 percent by weight or less or about 1.0 percent by weight or less based on the weight of the composition.

These compositions may contain an additive to improve scratch resistance. Any additive which improves scratch resistance may be utilized. Exemplary scratch resistance additives may include, silicates, aluminas, zirconias, carbides, oxides, nitrides or any other fillers with high hardness. Classes of scratch resistance additives may include alumina (e.g., alpha alumina), silica, zirconia, boron carbide, silicon carbide, cerium oxide, glass, diamond, aluminum nitride, silicon nitride, yttrium oxide, titanium diboride, aluminosilicates (i.e. "Zeeospheres" from 3M), titanium carbide, combinations thereof, and the like. Classes of scratch resistance additives are silicates and aluminas. Exemplary scratch resistance additives may include nanometer sized silica fillers. The scratch resistance additives may have a particle size of about 10 micrometers or less or about 5 micrometers or less. The scratch resistance additives may be present in a sufficient amount to enhance the surface hardness and abrasion resistance of a coating and in an amount such that a homogeneous dispersion can be prepared. The scratch resistance additives may be present in an amount of about 0.1 percent by weight or greater of the composition or about 0.5 percent by weight or greater. The scratch resistance additives may be present in an amount of about 5 percent by weight or less of the composition, about 2 percent by weight or less or about 1 percent by weight or less.

These compositions may comprise an additive to improve surface slip properties. Any known composition that improves surface slip properties may be used. Exemplary surface slip additives may be a polyester modified polydimethyl siloxanes, waxes and the like. Exemplary waxes include those based on polyethylene, polytetrafluoroethylene or polypropylene wax dispersions in acrylate monomers, such as the EVERGLIDE™ or S-395 or SST series of products from Shamrock Technologies, or polyamide particles such as ORGASOL™ from Arkema, or montan wax with reactive acrylate groups, such as CERIDUST™ TP 5091 from Clariant, or CERAFLOUR™ wax powders from Byk-Chemie. The wax may be in powder form having a particle size which is smaller than the desired thickness of a coating prepared from the composition. The maximum particle size may be about 30 microns or less, about 25 microns or less, about 20 microns or less or about 15 microns or less. The wax may be highly crystalline. Exemplary waxes comprise a polyethylene, polypropylene, polyamide, polytetrafluoroethylene, or blends and/copolymers thereof. The wax may be crystalline polyethylene or polytetrafluoroethylene or blends of polyethylene with polytetrafluoroethylene. The surface slip additives may be present in an amount of about 0.1 percent by weight or greater of the composition or about 0.5 percent by weight or greater. The surface slip additives may be present in an amount of about 5 percent by weight or less of the composition, about 2 percent by weight or less or about 1 percent by weight or less.

Disclosed is a composition which comprises one or more polyester macromers or a composition containing one or more polyester macromers as disclosed herein and one or more polyols having the residue of one or more 1,1-diester-1-alkenes disposed on at least one of its terminal ends in place of the hydroxyl groups. The residue of one or more 1,1-diester-1-alkenes may be disposed on at least two of its terminal ends in place of the hydroxyl groups. The residue of one or more 1,1-diester-1-alkenes may be disposed on substantially all of its terminal ends in place of the hydroxyl groups. The one or more polyols may have 2 or more chains and the residue of one or more 1,1-disubstituted alkenes at the terminal end of one or more of the chains. The polyol may be any polyol which can be transesterified using the methods disclosed herein. The polyols may be any polyol which imparts elasticity to cured and/or crosslinked coatings, films and other structures prepared from compositions containing the polyester macromers. Exemplary polyols include one or more polyether polyols, polysiloxane polyols, polycarbonate polyols, polyester polyols, or polybutadienyl polyols. The polyol may be one or more polyether polyols, polycarbonate polyols or polyester polyols. The polyol may be one or more polycarbonate polyols. The polyol may be di or tri functional. The composition containing one or more polyester macromers and one or more endcapped polyols may contain a sufficient amount of one or more polyester macromers to prepare a cured coating film or other structure. The polyester macromers are present in an amount of about 10 percent by weight or greater of the composition containing polyester macromers and polyols, about 20 percent by weight or greater or about 40 percent by weight or greater. The polyester macromers are present in an amount of about 80 percent by weight or less of the composition containing polyester macromers and polyols, about 60 percent by weight or less or about 40 percent by weight or less. The polyols are present in sufficient amount to introduce the desired flexibility to the cured and/or crosslinked coatings, films, fibers, particles or other structures prepared from the compositions. The polyols may be present in an amount of about 10 percent by weight or greater of the composition containing polyester macromers and polyols, about 20 percent by weight or greater or about 30 percent by weight or greater. The polyols may be present in an amount of about 30 percent by weight or less of the composition containing polyester macromers and polyols, about 20 percent by weight or less or about 10 percent by weight or less. The composition containing polyester macromers and polyols may further include one or more solvents. The one or more solvents are present to enhance the delivery of the composition containing polyester macromers and polyols. Exemplary classes of solvents are disclosed hereinbefore. The one or more solvents are present in sufficient amount to enhance the delivery of the composition containing polyester macromers and polyols. The solvents may be present in an amount of about 5 percent by weight or greater of the composition containing polyester macromers polyols and the solvents, about 10 percent by weight or greater or about 20 percent by weight or greater. The solvents may be present in an amount of about 40 percent by weight or less of the composition containing polyester macromers, polyols and the solvents, about 30 percent by weight or less or about 20 percent by weight or less. The composition containing polyester macromers and polyols may contain any of the ingredients disclosed herein as useful in the polyester macromer containing compositions.

The polyester macromer compositions disclosed herein can be used to prepare coatings, films, fibers, particles and other structures. Such structures may be cured and or crosslinked. The crosslinked compositions may be crosslinked through the alkene groups pendant from the macromer chains. The crosslink may be a direct bond between the alkene groups of adjacent macromer chains. The macromer chains may be included in prepolymer or polymer chains. The macromer chains may be crosslinked through any compound having unsaturation that polymerizes by anionic or free radical polymerization. The polyester macromer chains may be crosslinked through 1,1-diester alkenes wherein the crosslinks comprise the residue of the 1,1-diester alkenes. The polyester macromer chains may be crosslinked through multifunctional monomers wherein the crosslinks comprise the residue of the multifunctional monomers. The crosslinks between chains may be illustrated by formula 16:

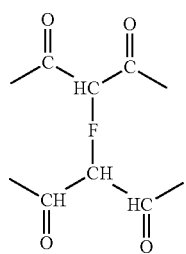

16 wherein F is separately in each occurrence a direct bond, the residue of a compound that polymerizes with an unsaturated group by anionic polymerization or free radical polymerization. F may be separately in each occurrence a direct bond, the residue of a 1,1-diester-1-alkene or a multifunctional monomer. The crosslink density of a crosslinked composition containing the polyester macromers may be any such density that provides the desired properties of the composition.

The polyester macromers and compositions containing them may undergo polymerization when exposed to basic cure initiators. If applied to the surface of a substrate that is basic the polyester macromers will cure via anionic polymerization. Polyester macromers and compositions containing the polyester macromers can undergo cure if contacted with a composition containing basic materials as a polymerization activator. The polymerization activator and methods of delivering the polymerization activator are disclosed in Malofsky U.S. Pat. No. 9,181,365, incorporated herein by reference in its entirety for all purposes. The polymerization activator is at least one of a base, a base enhancer, a base creator, or a base precursor. In certain embodiments, the polymerization activator comprises a basic material selected from a strong base (pH over 9), a moderately strong base (pH from 8-9), or a (mildly basic) weak base (pH from over 7 to 8), or a combination thereof. In other embodiments, the polymerization activator comprises a basic material selected from an organic material, an inorganic material or an organometallic material, or a combination thereof. The polymerization activator is at least one member selected from: sodium acetate; potassium acetate; acid salts of sodium, potassium, lithium, copper, and cobalt; tetrabutyl ammonium fluoride, chloride, and hydroxide; an amine whether primary, secondary or tertiary; an amide; salts of polymer bound acids; benzoate salts; 2,4-pentanedionate salts; sorbate salts; propionate salts; secondary aliphatic amines; piperidine, piperazine, N-methylpiperazine, dibutylamine, morpholine, diethylamine, pyridine, triethylamine, tripropylamine, triethylenediamine, N,N-dimethylpiperazine, butylamine, pentylamine, hexylamine, heptylamine, nonylamine, decylamine; salts of amines with organic monocarboxylic acids; piperidine acetate; metal salt of a lower monocarboxylic acid; copper(II) acetate, cupric acetate monohydrate, potassium acetate, zinc acetate, zinc chloracetate, magnesium chloracetate, magnesium acetate; salts of acid containing polymers; salts of polyacrylic acid copolymers, or pigments having a basic character. In certain embodiments, the polymerization activator is encapsulated in a wax, or is provided in inactive engagement with the polymerizable composition by chemical inactivation.

Disclosed herein is a polymerizable system comprising: a polymerizable composition; and polymerization activator physically separated from the polymerizable composition; wherein the polymerizable composition comprises polyester macromers or compositions containing the polyester macromer; and wherein the polymerization activator is able to initiate polymerization upon contact with the polymerizable composition without substantial mixing. The polymerization activator may be physically separated from the polymerizable composition, the physical separation is achieved by storing the activating agent and the polymerizable composition in separate locations within an applicator means. In exemplary embodiments, the applicator means is an aerosol spray device. In other embodiments, the physical separation is achieved by initially applying the polymerization activator to at least a portion of a substrate, followed by applying the polymerizable composition to the portion of the substrate. In still other embodiments, the physical separation is achieved by providing the polymerization activator in or on at least a portion of a substrate. The polymerization activator may be physically separated from the polymerizable composition, the polymerization activator is in an inert state and wherein the polymerizable system further comprises a converting agent able to convert the polymerization activator from the inert state to an active state. The basic polymerization initiator may be encapsulated in a composition that can be subjected to a process that releases the initiator. An encapsulated initiator particle includes an initiator matrix. The initiator matrix includes a first cured composition formed of one or more 1,1-disubstituted alkene compounds and one or more polymerization initiators substantially encapsulated by the first cured composition. Exemplary compositions are disclosed in U.S. Pat. No. 9,334,430 incorporated herein by reference in its entirety for all purposes.

Disclosed is a composition comprising a composition containing one or more polyester macromers as disclosed herein in one part and in a second part one or more compounds having basic character sufficient to initiate anionic polymerization of the polyester macromers; wherein when the two parts are combined the polyester macromers undergo curing. Any of the basic materials disclosed herein may be used. The one or more compounds having basic character may be one or more amines or polyamines. The one or more compounds having basic character may be one or more polyalkyleneimines, such as polyethyleneimines.

The polyester macromers and compositions containing them may be used in the preparation of polyester based structures, such as coatings on substrates, films, fibers, adhesives and the like. Disclosed are coatings, films, fibers, particles and the like containing polyester macromers or the residue of the polyester macromers. A coating containing polyester macromers or the residue of the polyester macromers can be disposed on one or more surfaces or a portion thereof of a substrate. The films, coatings, or other structures may be cured and/or crosslinked. The films or coatings may have a thickness of about 0.01 micrometers or greater, about 0.04 micrometers or greater or about 0.1 micrometers or greater. The coating may be cured and/or crosslinked. The coating may have a thickness of about 160 micrometers or less, about 100 micrometers or less, about 80 micrometers or less or about 60 micrometers or less, about 20 micrometers or less or about 1 micrometer or less. Disclosed are articles comprising a substrate with a coating comprising one or more polyester macromers or a composition containing one or more polyester macromers applied to one or more surfaces.

Disclosed are articles comprising substrates containing base coats on the substrates with coatings containing polyester macromers disclosed herein disposed on the base coats. The base coats may have a basic character which is sufficient to cure and/or crosslink the polyester macromers. The coatings containing the polyester macromers may be clear and function as clear coats.

The polyester macromers or compositions containing them may be added to any composition containing the ingredients to prepare polyesters so as to introduce alkene units into the backbone. The compositions comprise diols and diesters known to those skilled in the art of preparing polyesters. The polyester macromers or compositions containing them may be added to blends containing polyesters to add the alkene functionality. The compositions containing the polyester macromers or compositions containing them may be crosslinked as disclosed herein.

The polyester macromers may be prepared from polyols, diols, and diesters. The di-esters include one or more 1,1-diester-1-alkenes and may include dihydrocarbyl dicarboxylates. The final structure of the polyester macromers may be determined by the ratios of reactants and the sequence of synthesis of intermediates which are disclosed hereinbefore; including multifunctional monomers, diol 1,1-diester-1-alkene adducts, and multifunctional monomers. The intermediates and the polyester macromers may be prepared by transesterification. The polyols having greater than two hydroxyl groups and diols function to initiate the polyester macromer chains. The diols also function to react with the diesters to form the macromer chains. The 1,1-diester-1-alkenes react with the polyols and diols to form the macromer chains and to introduce pendant alkene groups into the macromer chains. The dihydrocarbyl dicarboxylates function to react with the polyols and diols to form the macromer chains and to spread out the pendant alkene groups on the macromer chains. The polyester macromers may be prepared by contacting the polyol, diols and diesters and subjecting them to transesterification conditions. The resulting polyester macromers may have somewhat random and uncontrolled structure. It may be desirable to prepare intermediates and use the intermediates to prepare the polyester macromers as the use of intermediates allow for control of the final structure.

The multifunctional monomers may be prepared by contacting one or more polyols with an equivalents excess of one or more 1,1-diester 1-alkenes in the presence of a transesterification catalyst under conditions such that one or more multifunctional monomers are formed wherein the multifunctional monomers contain the one or more polyols having two or more of their hydroxyl groups replaced with the residue of the one or more 1,1-diester 1-alkenes. The ratio of equivalents of one or more 1,1-diester 1-alkenes to one or more polyols maybe about 2:1 or greater or about 4:1 or greater. The ratio of equivalents of one or more 1,1-diester 1-alkenes to one or more polyols maybe about 5:1 or less or about 3:1 or less. The multifunctional monomers may be used to control the number of chains in the polyester macromers and/or to form the polyester macromer chains in a controlled manner. The polyol capped dihydrocarbyl dicarboxylates may be prepared by contacting the one or more dihydrocarbyl dicarboxylates with an excess of one or more polyols in the presence of a transesterification catalyst under conditions such that one or more dihydrocarbyl dicarboxylates having the residue of a polyol bonded to each of the carbonyl groups is prepared. The ratio of equivalents of one or more diols to one or more dihydrocarbyl dicarboxylates maybe about 2:1 or greater. The ratio of equivalents of one or more diols to one or more dihydrocarbyl dicarboxylates maybe about 4:1 or less or about 3:1 or less.

Disclosed is a method comprising: contacting one or more polyols with an equivalents excess of one or more 1,1-diester 1-alkenes in the presence of a transesterification catalyst under conditions such that one or more multifunctional monomers are formed wherein the multifunctional monomers contain the one or more polyols having two or more of their hydroxyl groups replaced with the residue of the one or more 1,1-diester 1-alkenes; and contacting the multifunctional monomers with an additional amount of the one or more polyols, with the proviso that the polyols are diols, or with one or more second polyols which are diols, in the presence of a transesterification catalyst under conditions such that one or more polyester macromers are prepared which contain one or more chains of the residue of one or more diols and one or more 1,1-diester-1-alkenes wherein the residue of the one or more diols and the one or more 1,1-diester-1 alkenes alternate along the chain and at least one terminal end comprises the residue of one of the 1,1-diester-1 alkenes and wherein one or more terminal ends may comprise the residue of one or more diols. The multifunctional monomers and an additional amount of the one or more polyols or with one or more second polyols are contacted with one or more compounds comprising one or more dihydrocarbyl dicarboxylates having the residue of a polyol bonded to each of the carbonyl groups such that one or more polyester macromers are prepared wherein at least some to the polyester macromers contain the residue of the one or more the dihydrocarbyl dicarboxylates in their backbone. The one or more compounds comprising the one or more dihydrocarbyl dicarboxylates having the residue of a polyol bonded to each of the carbonyl groups is prepared by contacting the one or more dihydrocarbyl dicarboxylates with an excess of one or more polyols in the presence of a transesterification catalyst under conditions such that one or more dihydrocarbyl dicarboxylates having the residue of a polyol bonded to each of the carbonyl groups is prepared.

Disclosed a method comprising: contacting one or more diols, one or more 1,1-diester 1-alkenes, and one or more dihydrocarbyl dicarboxylates in the presence of a transesterification catalyst under conditions that one or more polyester macromers are prepared which contain one or more chains of the residue of one or more diols, one or more dihydrocarbyl dicarboxylates and one or more 1,1-diester-1-alkenes wherein the residues of each are disposed in a random manner along the chain and at least one terminal end comprises the residue of one of the 1,1-diester-1 alkenes and wherein one or more terminal ends may comprise the residue of one or more diols.

Disclosed is a method comprising: contacting one or more polyols with an equivalents excess of one or more 1,1-diester 1-alkenes in the presence of a transesterification catalyst under conditions such that one or more multifunctional monomers are formed wherein the multifunctional monomers contain the one or more polyols having at least two of their hydroxyl groups replaced with the residue of the one or more 1,1-diester 1-alkenes; and contacting the one or more multifunctional monomers one or more diols, one or more 1,1-diester 1-alkenes, and one or more dihydrocarbyl dicarboxylates in the presence of a transesterification catalyst under conditions that one or more polyester macromers are prepared which contain one or more chains of the residue of one or more diols, one or more dihydrocarbyl dicarboxylates and one or more 1,1-diester-1-alkenes wherein the residues of each are disposed in a random manner along the chain and at least one terminal end comprises the residue of one of the 1,1-diester-1 alkenes and wherein one or more terminal ends may comprise the residue of one or more diols.

Disclosed is a method comprising: contacting one or more multifunctional monomers which contain the one or more polyols having their hydroxyl groups replaced with the residue of the one or more 1,1-diester 1-alkenes; one or more compounds comprising a dihydrocarbyl dicarboxylates having the residue of a polyol bonded to each of the carbonyl groups; and one or more polyols in the presence of a transesterification catalyst under conditions such that one or more polyester macromers are prepared which contain one or more chains of the residue of the one or more polyols, the one or more 1,1-diester-1-alkenes, and the one or more compounds comprising a dihydrocarbyl dicarboxylates having the residue of a polyol bonded to each of the carbonyl groups and at least one terminal end comprises the residue of one of the 1,1-diester-1 alkenes and wherein one or more terminal ends may comprise the residue of one or more diols.

In the methods disclosed the one or more polyols or second polyols may be diols. The one or more dihydrocarbyl dicarboxylates comprise one or more of aromatic dicarboxylates, aliphatic dicarboxylates and cycloaliphatic dicarboxylates. The oxygens from the hydroxyl groups on the diols and polyols may be bonded to aliphatic carbon atoms.

Transesterification is an equilibrium process and is typically performed under conditions to remove the byproduct formed during the exchange, meaning the product formed by the hydrocarbyl moieties leaving the esters undergoing transesterification. In some desired embodiments the hydrocarbyl moieties leaving the ester group of the first ester compound are smaller than the hydrocarbyl moieties replacing them so as to make the byproducts more volatile than the transesterified ester compounds. The smaller byproducts will generally be more volatile than the transesterified ester compound, which facilitates removal of the byproduct due to their volatile nature. The process disclosed can be used with any process conditions that remove the byproduct formed from the leaving hydrocarbyl moieties. Exemplary process conditions or steps that may be used to remove the byproduct formed from the leaving hydrocarbyl moieties may include one or more of the following: distillation, membrane transport, inert gas purge, application of a vacuum, and the like.

The transesterification reactions are typically performed in the presence of a catalyst. The transesterification catalyst may be an acid, an ester of such acid or an enzyme. The transesterification catalyst may be an enzyme. The transesterification catalyst may be a lipase enzyme. A transesterification process utilizing an enzyme is disclosed in US 2014/0329980, incorporated herein by reference for all purposes in its entirety.

The catalyst may be an acid or an ester thereof. The transesterification process using an acid or ester is disclosed in co-owned U.S. Pat. No. 9,416,091, incorporated herein by reference for all purposes in its entirety. Any acid or ester thereof that catalyzes transesterification while minimizing side reactions may be used. In some embodiments the acid or acid utilized to form an ester is an acid having a pKa in a polar aprotic solvent, such as acetonitrile or dioxane, as disclosed hereinafter. In particular the pKa is chosen to efficiently catalyze the transesterification reaction while minimizing side reaction and the concentration of catalyst in a reaction mixture. The acid used may have a pKa of about −5 or greater, about −3 or greater, or about 1.0 or greater. The acid used may have a pKa of about 14 or less, about 11 or less, or about 9 or less. The acid can be a Bronsted acid having a pKa as disclosed. The catalyst may be a superacid or an ester thereof. Superacid means an acid having an acidic strength greater than the strength of 100 percent sulfuric acid. Ester thereof, in the context of the acid catalysts, refer to compounds wherein the hydrogen on the acid is replaced with a hydrocarbyl group, preferably an alkyl group. Superacids are acids having a strength greater than the strength of 100 percent sulfuric acid, a pKa less than 100 percent sulfuric acid, that is less than 8, more preferably less than about 5, and most preferably less than about 2. The measurement of acid strength is based on Kutt et al. "Equilibrium Acidities of Super Acids," Journal of Organic Chemistry Vol 76 pages 391 to 395, 2011, published Dec. 17, 2010, which is incorporated herein by reference. Exemplary super acids include trifluoromethanesulfonic acid (triflic acid), sulfated tin oxide, triflated tin oxide, sulfated zirconia, triflated zirconia, and triflated HZSM-5. The most preferred super acids are triflic acid and fluorosulfonic acid.

Exemplary acid catalysts include triflic acid, fluorosulfonic acid, and sulfuric acid. For reactions requiring monosubstitution (only one hydroxyl group on the alcohol is being replaced by transesterification), weaker acids with pKa values equal to or higher than sulfuric acid may be desired. Examples of such acids include sulfuric acid or methanesulfonic acid. For reactions requiring disubstitution (two hydroxyl groups on the alcohol are being replaced by transesterification), stronger acids with pKa values equal to or lower than sulfuric acid may be desired. Examples of such acids include sulfuric acid, fluorosulfonic acid, and triflic acid. For reactions requiring polysubstitution (more than 2 hydroxyl groups on the alcohol), choice of acid catalysts can be similar to that for disubstitution reactions but reaction time may need to be increased. Esters of acids useful as catalysts include alkyl triflates.

The catalyst can be mixed with the reactants or can be supported on a substrate such as a membrane or an inert carrier such as a porous support structure (the catalysts can be heterogeneous). Catalysts which are not supported are commonly referred to as homogeneous. The catalyst can be used in any concentration that catalyzes the transesterification reaction. The amount of catalyst utilized for the reaction depends on the type of catalyst being chosen. The concentration of catalyst is about 2 molar equivalents or less per equivalent of the ester compounds undergoing transesterification; about 1 molar equivalents or less; about 0.5 molar equivalents or less; about 0.05 molar equivalents or less. The concentration of catalyst is about 0.001 molar equivalents or greater per equivalent of the ester compounds undergoing transesterification; and most preferably about 0.0015 molar equivalents or greater. Higher concentrations of catalysts than recited may be utilized. As disclosed in Malofsky et al., U.S. Pat. Nos. 8,609,885 and 8,884,051; and Malofsky et al. WO 2013/059473 the presence of acid in the 1,1-disubstituted alkene compounds recovered can present problems with respect to use of the compounds and low concentrations of acid in the products in use is desired. If high levels of acid are contained in the final product, additional purification or removal steps may be required. The amounts recited achieve the balance between efficient catalysis and the need for low acid concentrations in the product for use. The choice of polyol and/or diester compound and the relative moles of the polyol and the diester will impact the product of the process.

Where the reactants are liquid under reaction conditions it is desired to contact the reactants and catalysts in neat form (i.e., without a solvent or dispersant). If the use of a solvent is desired, a solvent that does not react with the reactants or the catalyst is preferred. Another consideration in the choice of solvents is the boiling point of the solvent chosen. The solvent may have a boiling point of about 15° C., preferably about 20° C., or higher than the temperature at which the reaction is conducted. Aprotic solvents are preferred and more preferred solvents are long chain alkanes having a boiling point above the reaction temperature as described; exemplary solvents are decane or dodecane.

The reactants are contacted at any temperature at which the transesterification will proceed. Preferably the reactants are contacted at a temperature of about 80° C. or greater or about 100° C. or greater. The reactants may be contacted at a temperature of about 160° C. or less, 140° C. or less, or about 130° C. or less.

The reactants are contacted for a sufficient time to prepare the desired transesterified product. It is preferred to perform the process such that the starting ester compound, such as a 1,1-disubstituted alkene compound, is substantially completely reacted with the polyol to prepare the desired product. The reactants may be contacted for about 1 hour or greater. The reactants may be contacted may be 8 hours or less or about 4 hour or less.

It is desired to perform the process under conditions that enhance contact of the diesters and polyol to allow the replacement of the original hydrocarbyl moieties on the ester groups of the diester. Some form of agitation is desired to enhance this contact. Exemplary methods of agitation include the use of stirrers, sparging with an inert gas, and the like. A preferred method is to use vigorous stirring and/or vigorous sparging with nitrogen.

The catalyst may be an enzyme. The transesterification reaction conditions comprise room temperature and atmospheric pressure; elevated temperature and atmospheric pressure; room temperature and under vacuum; elevated temperature and under vacuum; or any combination thereof. The transesterification step may be performed at a temperature of about 20° C. or greater, about 35° C. or greater or about 40° C. or greater. The transesterification step may be performed at a temperature of about 85° C. or less, about 70° C. or less or about 50° C. or less.

The transesterification reaction may be performed in the presence of free radical stabilizers and anionic polymerization inhibitors as described in Malofsky et al., U.S. Pat. Nos. 8,609,885 and 8,884,051; and Malofsky et al. WO 2013/059473, relevant parts incorporated herein by reference. To prevent production of polymeric products, it is desirable to include an acid which inhibits polymerization but does not significantly participate in catalysis of the transesterification. The acid used to inhibit polymerization may have a pKa less than 100 percent sulfuric acid. According to certain embodiments, stabilizers can be included in compositions containing the transesterified products to increase and improve the shelf life and to prevent spontaneous polymerization. Generally, one or more anionic polymerization stabilizers and or free-radical stabilizers may be added to the compositions. Anionic polymerization stabilizers are generally electrophilic compounds that scavenge electrons from the composition or growing polymer chain. The use of anionic polymerization stabilizers can terminate additional polymer chain propagation. Exemplary anionic polymerization stabilizers are acids, exemplary acids are carboxylic acids, sulfonic acids, phosphoric acids, and the like. Exemplary stabilizers include liquid phase stabilizers (e.g., methanesulfonic acid ("MSA")) and vapor phase stabilizers (e.g., trifluoroacetic acid ("TFA")). In some embodiments it is desirable to utilize relatively weak acids to inhibit polymerization. Generally such weak acids exhibit a pKa in acetonitrile of less than −1.5 or less than about 2. Exemplary acids used to inhibit anionic polymerization are alkyl substituted aryl sulfonic acids, such as dodecylbenzenesulfonic acid, p-toluenesulfonic acid, and the like. As the catalyst in the method of the invention is an acid a second anionic polymerization inhibitor may not be required in performing the method disclosed herein. It is desired to include a free radical stabilizer or polymerization inhibitor in performing the method disclosed herein. The concentrations of the stabilizers, or polymerization inhibitors, useful in the method are disclosed hereinafter.

Free radical stabilizers preferably include phenolic compounds (e.g., 4-methoxyphenol, mono methyl ether of hydroquinone ("MeHQ") butylated hydroxytoluene ("BHT")). Stabilizer packages for 1,1-disubstituted alkenes are disclosed in U.S. Pat. No. 8,609,885 and U.S. Pat. No. 8,884,051, each incorporated by reference. Additional free radical polymerization inhibitors are disclosed in U.S. Pat. No. 6,458,956 and are hereby incorporated by reference. Generally, only minimal quantities of a stabilizer are needed and, in certain embodiments only about 5000 parts-per-million ("ppm") or less can be included. In certain embodiments, a blend of multiple stabilizers can be included; for example, a blend of anionic stabilizers (MSA) and free radical stabilizers (MeHQ).

The one or more anionic polymerization stabilizers are present in sufficient amount to prevent premature polymerization. The anionic polymerization stabilizers may be present in an amount of about 1 ppm or less based on the weight of the first ester compound (1,1-disubstituted alkene), about 5 ppm by weight or greater, or about 10 ppm by weight or greater. The anionic polymerization stabilizers may be present in an amount of about 500 ppm by weight or less based on the weight of the ester compound, about 250 ppm by weight or less, or about 100 ppm by weight or less. The one or more free radical stabilizers may be present in sufficient amount to prevent premature polymerization. The free radical polymerization stabilizers may be present in an amount of about 10 ppm or less based on the weight of the ester compounds, about 100 ppm by weight or greater, or about 1000 ppm by weight or greater. The free radical polymerization stabilizers may be present in an amount of about 10,000 ppm by weight or less based on the weight of the ester compounds, about 8000 ppm by weight or less, or about 5000 ppm by weight or less.

Disclosed is a method comprising contacting a composition containing one or more polyester macromers with a surface of a substrate wherein the surface is at least mildly basic and forming a coating on the surface of the substrate comprising the composition containing the one or more polyester macromers. The substrate is comprised of material that is basic. The composition that contains a basic compound may be applied to the surface of the substrate before applying the composition containing one or more polyester macromers. The composition that contains a basic compound may comprise any compound disclosed herein as an anionic polymerization inhibitor useful with 1,1-diester-1-alkenes. Exemplary basic compounds include an amine, polyamine basic pigments or carboxylate salts. The composition that contains a basic compound may comprise a polyalkyleneimine. The method may further include exposing the substrate with the composition containing one or more polyester macromers to a temperature of about 20° C. or greater or about 50° C. or greater. The method may further include exposing the substrate to with a composition containing one or more polyester macromers to a temperature of about to 150° C. or less or about 120° C. or less. The time period for such exposure may be about 10 minutes or greater or 20 minutes or greater. The time period for such exposure may be 120 minutes or less, about 60 minutes or less or about 30 minutes or less. The exposure is performed under conditions such that the coating containing one or more polyester macromers disposed on the surface of the substrate is cured and/or crosslinked.

The polyester macromer containing coatings or films may cure and/or crosslink when exposed to certain conditions. When the coating or film are exposed to relatively strong bases and or elevated temperatures they cure and crosslink at the same time. If they are exposed to mildly basic materials at relatively low temperatures, less than about 50° C. or less than about 40° C. they may not completely cure or crosslink. Such coatings or films may be cured by exposure to elevated temperatures to cure as disclosed hereinbefore.

ILLUSTRATIVE EMBODIMENTS OF THE INVENTION

The following examples are provided to illustrate the invention, but are not intended to limit the scope thereof. All parts and percentages are by weight unless otherwise indicated.

A typical reaction procedure is described as follows: a three neck 100 mL round bottom flask with a distillation head, thermometer, vacuum adapter, and collection flask are assembled using high vacuum grade grease along with a heating mantle, thermocouple, and a magnetic stir bar. The reaction mixture is subjected to agitation typically ranging from 400-600 rpm. Vacuum is used to remove subsequent byproducts from the reaction mixture and the various pressures are indicated below along with the mix time in each case. In some cases, nitrogen gas is used to purge the mixture in lieu of vacuum and, if applicable, is indicated below. In each case, the mole equivalent is relative to the diethyl methylene malonate ("DEMM") monomer used.

NMR spectroscopy is employed using a 300 MHz NMR to analyze reaction mixtures. Samples were prepared using chloroform-d ($CDCl_3$) and hexamethyldisiloxane as an internal standard appearing at about 0 ppm. For 1,1-disubstituted alkene compounds with symmetrical substituents (e.g., DEMM), the reactive alkene functionality (i.e., the double bond) appears at about 6.45 ppm. For 1,1-disubstituted alkene compounds with asymmetrical substituents (e.g., ethyl pentyl methylene malonate or "EPMM"), the reactive alkene functionality appears as a doublet at about 6.45 ppm. In most cases, four NMR scans are run on each samples specimen with a 20 second delay between scans.

GC-MS is employed to determine conversion of starting materials to the desired transesterified product(s) and detect the presence of any byproducts. A helium gas (carrier gas) purge of about 1 mL/min is employed to aid the ionized in sample reaching the MS detector. Typical sample injection volumes of 1-2 µL of about 2-5% of the reaction mixture in dichloromethane ($CH_2Cl_2$) are used for injecting into the GC-MS instrument. The GC-MS profile method involves maintaining the oven at 100° C., followed by a ramp of 15° C./min to 250° C. Typical run times range from 18-23 minutes. Retention times of 1,1-disubstituted alkene compounds, based on the above mentioned method, range from 4.5-17 min and are strongly dependent on the substituents and the ease of ionization of the particular molecule in the GC chamber.

For the examples herein disclosed, the conversion of starting reactant materials (i.e., a first ester or 1,1-disubstituted alkene compound) to the desired transesterified 1,1-disubstituted alkene compounds with the use of a suitable transesterification reagent (i.e., an alcohol) is calculated as follows unless otherwise indicated: The starting weight of the limiting reagent in each reaction is used as the baseline measurement and constitutes 100% theoretical maximum conversion. Conversion is then obtained by dividing the percent composition of the transesterified product provided via GC-MS in the final reaction mixture by the theoretical maximum conversion.

Ingredients and Products
Pentane Diol
DEM Diethyl malonate
DEMM Diethyl methylene malonate (diethyl 1-methylene-1,1-dicarboxylate)
MeHQ Mono methyl ether hydroquinone
MSA Methanesulfonic acid
Catalyst CALB Lipase Enzyme Example 1—Preparation of Di-Functional Monomer from Pentane Diol and DEMM A round bottom flask is charged with DEMM (172 g, 1 mol), pentanediol (26 g, 0.25 mol) and CALB lipase enzyme (8.6 g) (purchased from CLEA) 5 weight percent based on DEMM. The round bottom flask is placed on a rotovap preheated to 45° C. and pressure of 150 mm Hg is applied. After 1 hour the reaction is checked for completion by GCMS and HNMR. Once the pentanediol has been consumed, the reaction has gone to completion. The product mixture is about a 65/35 mixture of difunctional monomer and DEMM. The reaction mixture is filtered to remove enzyme. Charge a 3 neck round bottom flask equipped with mechanical agitator, thermometer and a condenser is charged with the reaction mixture formed. The reaction mixture is distilled at 65° C. and a pressure<0.800 mmHg for 2 hours or until the amount of difunctional monomer is less than 65 percent by weight of the solution. The typical product composition is: 67% DEMM-pentanediol crosslinker and 33% DEMM.

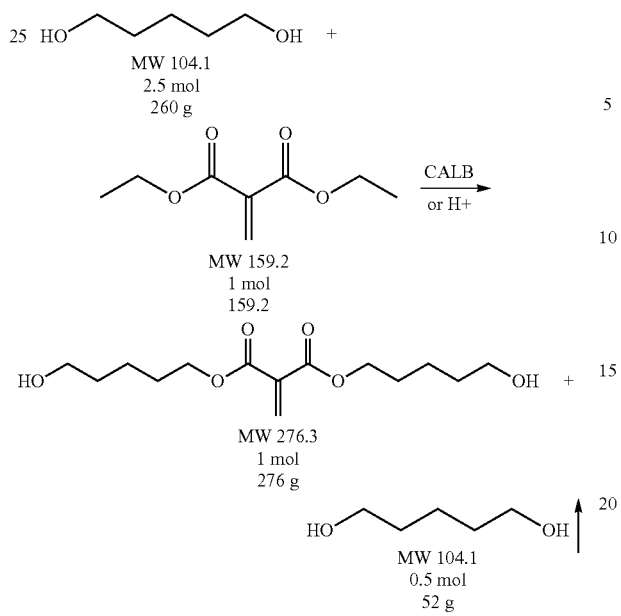

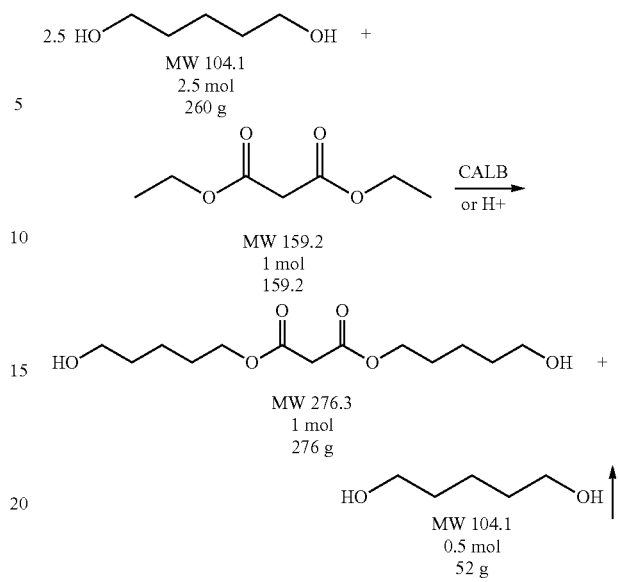

Example 2—Endcapping Diethyl Malonate with Pentane Diol

A round bottom flask is charged with pentanediol (260 g 2.5 mol), DEM (159 g, 1 mol) and CALB lipase enzyme (18 g) (purchased from CLEA), 7 weight percent based on pentanediol. The round bottom flask is placed on a rotovap and preheated to 45° C. and a pressure of 150 mm Hg is applied. After 1 hour the reaction is checked for completion by GCMS and HNMR. Once the DEM has been consumed, the reaction has gone to completion. The reaction mixture is filtered to remove enzyme. A 3 neck round bottom flask equipped with mechanical agitator, thermometer and a condenser is charged with the reaction mixture which is distilled at 100° C. and less than 0.800 mmHg for 2 hours or until the amount of pentanediol is about 10 weight percent of the reaction mixture (as determined by GCMS). The typical product composition is: about 90 percent by weight or pentanediol capped diethyl malonate and about 10 percent by weight pentanediol.

Example 3—Preparation of Polyester Macromer

A round bottom flask is charged with DEMM-pentanediol difunctional monomer (142 g, 0.4 mol) and pentanediol capped diethyl malonate (27.6 g 0.1 mol), diethyl methylene malonate, (70 g, 0.4 mol), pentane diol (2.7 g, 0.025 mol) and CALB lipase enzyme (10 g) 7 weight percent based on DEMM-pentanediol difunctional monomer. The round bottom flask is placed on a rotovap preheated to 45° C. and at a pressure of 150 mm Hg. After 1 hour the reaction mixture is checked for completion (disappearance of pentanediol-difunctional monomer) by GCMS. The reaction mixture is filtered to remove the enzyme. The resulting solution is examined by GPC. The product composition is generally comprised of the following: 60-75 weight percent of polyester macromer, 20-30 weight percent of pentanediol-difunctional monomer, 0-10 weight percent of DEMM. 100 ppm MEHQ and 10 ppm MSA are added to the final product. MSA is accurately measured out from a 1 percent by weight MSA: DEMM solution). This reaction is illustrated by the equation:

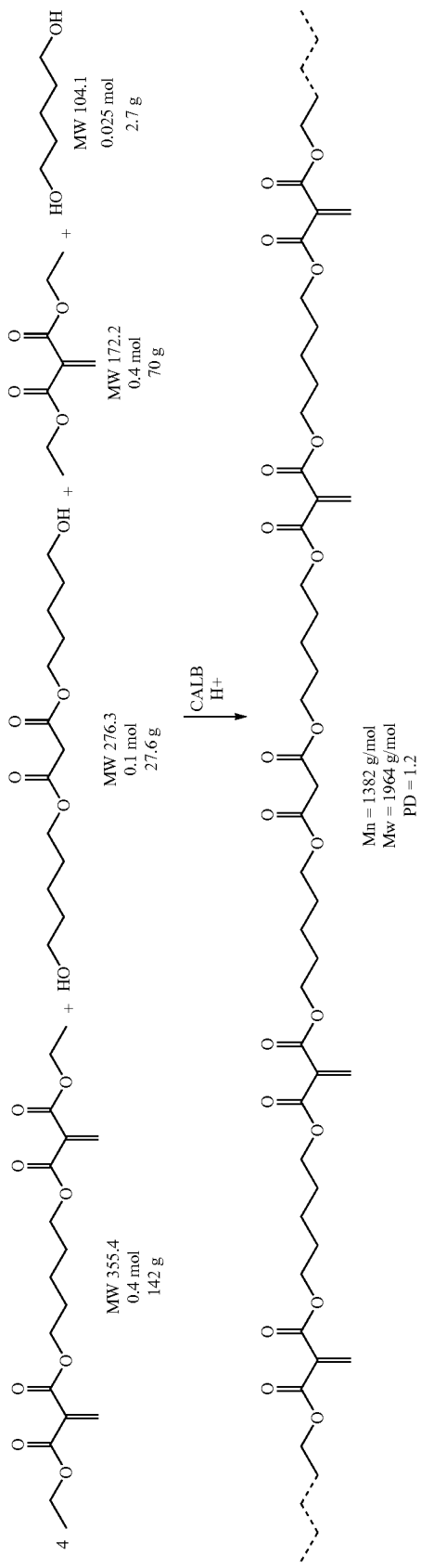

Example 4—Preparation of Polyester Macromer

A round bottom flask is charged with DEMM-pentanediol difunctional monomer (142 g, 0.4 mol), diethyl methylene malonate, (70 g, 0.4 mol), pentane diol (10.8 g, 0.10 mol) and CALB lipase enzyme (10 g) 7 weight percent based on DEMM-pentanediol difunctional monomer. The round bottom flask is placed on a rotovap preheated to 45° C. at a pressure of 150 mm Hg. After 1 hour the reaction mixture is checked for completion (disappearance of pentanediol-difunctional monomer) by GCMS. The reaction mixture is filtered to remove the enzyme. The resulting solution is examined by GPC. The product composition is generally comprised of the following: 60-75 weight percent of polyester macromer, 20-30 weight percent of pentanediol-difunctional monomer, 0-10 weight percent of DEMM. 100 ppm MEHQ and 10 ppm MSA are added to the final product. MSA is accurately measured out from a 1 percent by weight MSA/DEMM solution). This is illustrated by the equation:

in bulk, the resultant polymer does not dissolve in dichloromethane (DCM), confirming the high degree of crosslinking.

Example 6—Preparation of Coatings and Testing of the Coatings

Steel panels from Q-Panel are coated to evaluate the properties of a number of coatings containing polyester macromers. A Meyer Rod RD 20 is used to draw down the coatings on a panel pre-initiated with a basic polymeric imine that functions as an initiator. The applied coating is cured in a forced air oven, for 20-30 minutes at 120° C. The coatings acquired full cure within that timeframe. The coated panels are tested for a number of properties, pencil hardness according to ASTM D3363, gloss according to ASTM D523, solvent resistance according to ASTM D7835, flexibility according to GMW 14829 and adhesion of the coating to the panels according to GMW 16746. The tested formulations are listed in Table 1.

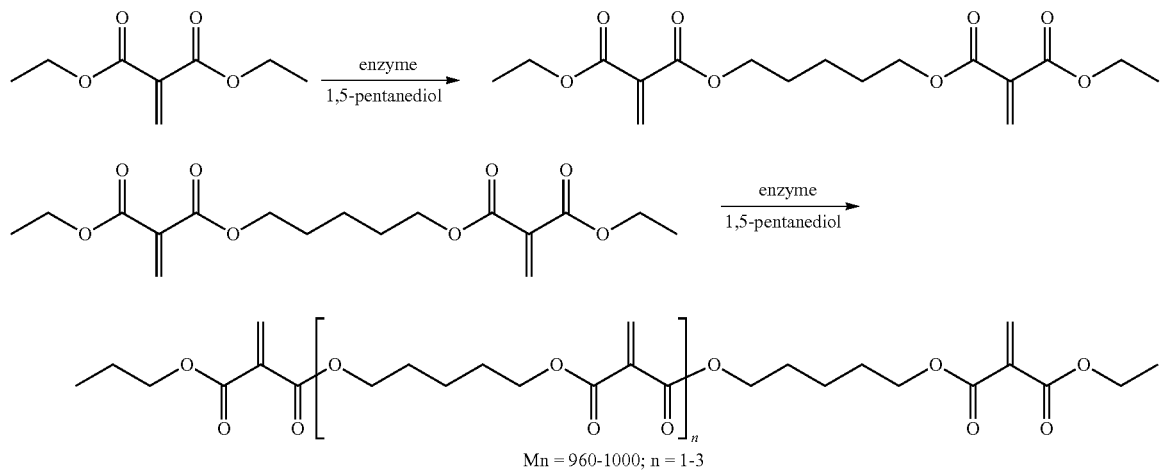

Mn = 960-1000; n = 1-3

Example 5—Methylene Malonate End Capped Polycarbonate Polyol 30 g of DEMM is charged along with 6 g of Pacapol F250 polycarbonate polyol (5:1 weight ratio) in a round bottom flask and mixed till the polyol dissolves or disperses into the DEMM monomer. Polycarbonate polyol typically takes longer to form a homogeneous mixture with DEMM in the reaction mixture and toluene can be used as a solvent for the reaction to avoid compatibility problems. 3 g of CLEA B4 enzyme catalyst (10% by weight of DEMM) is added to the reaction mixture. The round bottom flask is attached to a Rotary Evaporator maintained at 45° C. and rotated at 100 rpm for 2 hours under vacuum at 200 mm of Hg. At the end of the reaction, a small aliquot is taken for NMR analysis and the bulk of the reaction mixture is filtered using a cotton plug in a 100 ml syringe to remove the enzyme. This represents a blend of DEMM with end capped polycarbonate polyol in an approximate ratio of 75-25 by weight. Hexane is added to the reaction mixture as a good solvent for DEMM and a bad solvent for the polyol and end capped polyol. This allows the end capped polyol to be separated from excess DEMM of the reaction mixture. A portion of the reaction mixture or the concentrated end capped polyol is cured in an aluminum pan using tetramethyl guanidine TMG

| Ingredient | Amount g | % | Test Designation |
|---|---|---|---|
| Product of Example 1 | 10 | 100 | A |
| Product of Example 4 | 10 | 100 | B |
| Product of Example 4 | 8 | 80 | C |
| Polycarbonate Polyol endcapped according to Example 5 | 2 | 20 | C |
| Product of Example 3 | 10 | 100 | D |

The results are compiled in Table 2

| Test | Crosslinker | Adhesion | Flexibility |
|---|---|---|---|
| A | Alkane crosslinker | Fail | Fail |
| B | Polyester Crosslinker | Pass | Fail |
| C | Polyester Polyol blended with endcapped polycarbonate polyol according to Example 5 | Pass | Pass |
| D | Spacer in Backbone | Pass | Pass |

A coating of the composition of the product of Example 4 is applied to a substrate of cold rolled steel which is pre-initiated with a basic polymeric imine. The dry coating thickness is 40 micrometers. The applied coating is cured in an oven, for 20-30 minutes at 120° C. The coatings acquire full cure within that timeframe. The coated panels are tested for abrasion resistance according to a Taber Abrader Model 5750 using the following settings: CS-10 Weaser, 1100 gram load, 2 inch stroke length and speed of 75 cpm. The coatings remain intact to 2,500 total cycles before breakthrough to the substrates. Compared to the alkane crosslinker results of test Designation A 200 total cycles on the same instrument and same settings, this polyester coating shows significant improvement in abrasion resistance.

The coatings of examples 3 and 4 are tested for gloss according to ASTM D523. Each coating is measured at 20°, 60°, and 85°. The coatings exceed 70 Gloss Units (GU) for the 60°, and all the coatings are classified as high gloss. The coatings show a gloss reading of over 100 GU. The results are shown in FIG. 1.

The coatings of examples 1 and 4 are tested for solvent resistance to 2-butanone according to ASTM D 7835. The coating made with the alkane crosslinker from Example 1 can withstand about 70-80 single wipes. The coating made by the polyester in Example 4 can withstand more than 200 single wipes. The results are shown in FIG. 2.

The coatings of examples 1, 3 and 4 are tested for pencil hardness according to ASTM D 3363. Pencil hardness is performed using a BYK pencil tester. The scale for hardness does not exceed 9H. The coating made with the alkane crosslinker from Example 1 has a pencil hardness of 4H-6H. The coating made by the polyester in Example 3 has a pencil hardness of over 7H. The coating made by the polyester in Example 4 has a pencil hardness of over 8H. The results are shown in FIG. 3.

Any numerical values recited include all values from the lower value to the upper value in increments of one unit provided that there is a separation of at least 2 units between any lower value and any higher value. For values which are less than one, one unit is considered to be 0.0001, 0.001, 0.01 or 0.1 as appropriate. These are only examples of what is specifically intended and all possible combinations of numerical values between the lowest value, and the highest value enumerated are to be considered to be expressly stated in this application in a similar manner. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

The invention claimed is:

1. A composition comprising a polyester macromer containing one or more chains of repeating units comprising the residue of one or more diols and one or more diesters wherein the residue of the one or more diols and the one or more diesters alternate along the chain and a portion of the diesters are 1,1-diester-1-alkenes and at least one terminal end comprises the residue of one of the 1,1-diester-1 alkenes and wherein one or more terminal ends may comprise the residue of one or more diols wherein the number of repeating units in each chain is 3 or greater wherein the polyester macromers exhibit a number average molecular weight of about 600 to about 3000.

2. A composition according to claim 1 wherein the polyester macromer contains three or more alternating chains of the residue of one or more diols and one or more diesters wherein each of the chains are bonded at one end to an oxygen of the residue of a polyol having three or more of the oxygen atoms.

3. A composition according to claim 1 wherein the polyester macromer corresponds to Formula 1

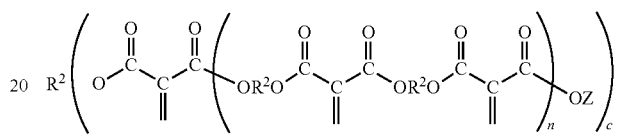

wherein Z is separately in each occurrence —R$^2$OH or —R$^1$;

R$^1$ is separately in each occurrence a hydrocarbyl group which may contain one or more heteroatoms;

R$^2$ is separately in each occurrence a hydrocarbylene group having two or more bonds to oxygen atoms wherein the hydrocarbylene group may contain one or more heteroatoms;

c is an integer of 1 or more; and n is an integer of about 1 to 3.

4. A composition according to claim 2 wherein the one or more chains further comprise the residue of one or more dihydrocarbyl dicarboxylates.

5. A composition according to claim 4 wherein the polyol corresponds to the formula;

the 1,1-diester-1-alkenes correspond to the formula;

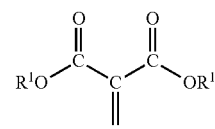

wherein the one or more dihydrocarbyl dicarboxylates correspond to the formula:

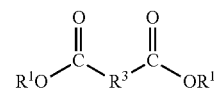

wherein R$^1$ is separately in each occurrence a hydrocarbyl group which may contain one or more heteroatoms;

R$^2$ is separately in each occurrence a hydrocarbylene group having two or more bonds to oxygen atoms wherein the hydrocarbylene group may contain one or more heteroatoms;

R³ is separately in each occurrence a hydrocarbylene group having two bonds to the carbonyl groups of the diester wherein the hydrocarbylene group may contain one or more heteroatoms; and c is an integer of 1 or more.

6. A composition comprising a polyester macromer containing one or more chains of repeating units comprising the residue of one or more diols and one or more diesters wherein the residue of the one or more diols and the one or more diesters alternate along the chain and a portion of the diesters are 1,1-diester-1-alkenes and at least one terminal end comprises the residue of one of the 1,1-diester-1 alkenes and wherein one or more terminal ends may comprise the residue of one or more diols wherein the number of repeating units in each chain is 3 or greater wherein the number of repeating units in each chain is from 3 to 10.

7. A composition according to claim 6 wherein the number of repeating units in each chain is from 3 to 8.

8. A composition according to claim 6 wherein the number of repeating units in each chain is from 3 to 6.

9. A composition according to claim 1 wherein the polydispersity of the polyester macromers is about 1.05 to about 2.5.

10. A composition according to claim 1 wherein the polydispersity of the polyester macromers is about 1.05 to about 1.5.

11. A composition according to claim 4 wherein the ratio of the residue of 1,1-diestersubstituted-1-alkenes to the residue of dihydrocarbyl dicarboxylates is about 15:1 to about 1:1.

12. A composition according to claim 4 wherein the ratio of the residue of 1,1-diestersubstituted-1-alkenes to the residue of dihydrocarbyl dicarboxylates is about 10:1 to about 6:1.

13. A composition according to claim 1 wherein the polyester macromers exhibit a number average molecular weight of about 600 to about 2000.

14. A composition according to claim 3 wherein:
$R^1$ is separately in each occurrence alkyl, alkenyl, cycloalkyl, alkyl heterocyclyl, aryl, aralkyl, alkaryl, heteroaryl, or polyoxyalkylene, or both of the $R^1$s form a 5-7 membered cyclic or heterocyclic ring; and
$R^2$ is separately in each occurrence alkylene, alkenylene, cycloalkylene, alkyl heterocyclylene, arylene, aralkylene, alkarylene, heteroarylene, or polyoxyalkylene.

15. A composition according to claim 3 wherein:
$R^1$ is separately in each occurrence $C_{1-15}$ alkyl, $C_{2-15}$ alkenyl, $C_{3-9}$ cycloalkyl, $C_{2-20}$ heterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene, or both of the $R^1$ groups form a 5-7 membered cyclic or heterocyclic ring
$R^2$ is be separately in each occurrence a $C_{2-8}$ alkylene group;
wherein the recited groups may be substituted with one or more halo alkylthio, alkoxy, hydroxyl, nitro, azido, cyano, acyloxy, carboxy, or ester groups.

16. A composition according to claim 3 wherein:
$R^1$ is separately in each occurrence a $C_{1-4}$ alkyl.

17. A composition according to claim 5 wherein:
$R^1$ is separately in each occurrence alkyl, alkenyl, cycloalkyl, alkyl heterocyclyl, aryl, aralkyl, alkaryl, heteroaryl, or polyoxyalkylene, or both of the $R^1$s form a 5-7 membered cyclic or heterocyclic ring;
$R^2$ is separately in each occurrence alkylene, alkenylene, cycloalkylene, heterocyclylene, arylene, aralkylene, alkarylene, heteroarylene, or polyoxyalkylene;
wherein the recited groups of $R^1$ and $R^2$ may be substituted with one or more substituents.

18. A composition according to claim 5 wherein:
$R^1$ is separately in each occurrence $C_{1-15}$ alkyl, $C_{2-15}$ alkenyl, $C_{3-9}$ cycloalkyl, $C_{3-20}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene, or both of the $R^1$ groups form a 5-7 membered cyclic or heterocyclic ring
$R^2$ is separately in each occurrence a $C_{2-8}$ alkylene group;
$R^3$ is separately in each occurrence $C_{8-14}$ arylene, $C_{8-12}$ cycloalkylene, $C_{1-12}$ alkylene or $C_{2-12}$ alkenylene;
wherein the recited groups of $R^1$ and $R^2$ may be substituted with one or more halo alkylthio, alkoxy, hydroxyl, nitro, azido, cyano, acyloxy, carboxy, or ester groups.

19. A composition according to claim 5 wherein:
$R^1$ is separately in each occurrence a $C_{1-4}$ alkyl, and,
$R^3$ is methylene.

* * * * *